US010290480B2

(12) United States Patent
Crowell et al.

(10) Patent No.: US 10,290,480 B2
(45) Date of Patent: May 14, 2019

(54) METHODS OF RESOLVING ARTIFACTS IN HADAMARD-TRANSFORMED DATA

(71) Applicant: Battelle Memorial Institute, Richland, WA (US)

(72) Inventors: Kevin Crowell, Richland, WA (US); Spencer A. Prost, Tempe, AZ (US)

(73) Assignee: Battelle Memorial Institute, Richland, WA (US)

( * ) Notice: Subject to any disclaimer, the term of this patent is extended or adjusted under 35 U.S.C. 154(b) by 1075 days.

(21) Appl. No.: 13/866,686

(22) Filed: Apr. 19, 2013

(65) Prior Publication Data

US 2014/0025314 A1    Jan. 23, 2014

Related U.S. Application Data

(60) Provisional application No. 61/800,822, filed on Mar. 15, 2013, provisional application No. 61/673,320, filed on Jul. 19, 2012.

(51) Int. Cl.
*H01J 49/00* (2006.01)
*G06F 19/00* (2018.01)
(52) U.S. Cl.
CPC ........ *H01J 49/0036* (2013.01); *G06F 19/703* (2013.01)
(58) Field of Classification Search
USPC ........................................ 250/281, 282, 287
See application file for complete search history.

(56) References Cited

U.S. PATENT DOCUMENTS 4,084,136 A    4/1978 Libby et al.
5,396,065 A    3/1995 Myerholtz et al.
(Continued)

FOREIGN PATENT DOCUMENTS

WO    WO 2008/112351 A2    9/2008
WO    WO 2008/112351 A3    9/2008
WO    WO 2015/134190 A1    9/2015

OTHER PUBLICATIONS

International Search Report for PCT/US2013/042072 dated Nov. 29, 2013, 2 pages.
(Continued)

*Primary Examiner* — Lam S Nguyen
(74) *Attorney, Agent, or Firm* — Klarquist Sparkman, LLP

(57) ABSTRACT

Apparatus and methods are disclosed for processing data transformed according to an invertible transform (e.g., using a Hadamard transform) multiplexing scheme. In one example of the disclosed technology, a computer-implemented method includes generating transformed data by applying a Hadamard transform to intensity data generated by modulating input of analytes into a mass spectrometer according to a pseudorandom sequence (PRS). The exemplary method further includes identifying at least one pair of symmetric intensity peaks in the transformed data based on the PRS and removing data associated with the pair of symmetric peaks from the transformed data to produce modified data, which can be used to identify, characterize, and/or quantify the composition of the sample. In some examples, the exemplary method further includes validating peaks in the transformed data based on comparing the location of peaks in the untransformed intensity data.

32 Claims, 22 Drawing Sheets

(56) References Cited

U.S. PATENT DOCUMENTS

| | | | |
|---|---|---|---|
| 5,627,639 A | 5/1997 | Mende et al. | |
| 6,300,626 B1* | 10/2001 | Brock | H01J 49/0027 250/287 |
| 6,870,157 B1* | 3/2005 | Zare | H01J 49/0027 250/281 |
| 6,900,431 B2* | 5/2005 | Belov | H01J 49/0027 250/282 |
| 6,958,473 B2 | 10/2005 | Belov et al. | |
| 7,170,053 B2 | 1/2007 | Shvartsburg et al. | |
| 7,339,521 B2* | 3/2008 | Scheidemann | H01J 49/107 342/179 |
| 7,541,576 B2 | 6/2009 | Belov et al. | |
| 2001/0001616 A1 | 5/2001 | Rakib et al. | |
| 2002/0070338 A1 | 6/2002 | Loboda | |
| 2003/0055573 A1 | 3/2003 | Legore et al. | |
| 2004/0132454 A1 | 7/2004 | Trott et al. | |
| 2004/0144918 A1 | 7/2004 | Zare et al. | |
| 2004/0183007 A1 | 9/2004 | Belov et al. | |
| 2005/0001163 A1 | 1/2005 | Belov et al. | |
| 2005/0119868 A1 | 6/2005 | Scheidemann et al. | |
| 2005/0133712 A1 | 6/2005 | Belov et al. | |
| 2006/0054804 A1 | 3/2006 | Wexler | |
| 2006/0219889 A1 | 10/2006 | Shvartsburg et al. | |
| 2007/0081158 A1 | 4/2007 | Brady et al. | |
| 2007/0143319 A1* | 6/2007 | Malek | H01J 49/0036 |
| 2008/0185513 A1 | 8/2008 | Belov et al. | |
| 2009/0110033 A1 | 4/2009 | Shattil | |
| 2009/0250607 A1 | 10/2009 | Staats et al. | |
| 2010/0324834 A1 | 12/2010 | Treptow et al. | |
| 2013/0048852 A1 | 2/2013 | Verenchikov | |
| 2014/0316718 A1 | 10/2014 | Crowell et al. | |

OTHER PUBLICATIONS

Written Opinion for PCT/US2013/42072 dated Nov. 29, 2013, 5 pages.
Kupce et al., "Two-dimensional Hadamard Spectroscopy," *Journal of Magnetic Resonance*, vol. 162, pp. 300-310 (Nov. 2003).
Belov, M.E., et al., Dynamically Multiplexed Ion Mobility Time-of-Flight Mass Spectrometry, Analytical Chemistry, 80, 2008, 5873-5883.
Braun, K.L., et al., Fast Hadamard transform capillary electrophoresis for on-line, time-resolved monitoring, Analytical Chemistry, 78, 2006, 1628-1635.
Clowers, B. H., et al., Enhanced Ion Utilization Efficiency Using an Electrodynamic Ion Funnel Trap as an Injection Mechanism for Ion Mobility Spectrometry, Analytical Chemistry, 80, 2008, 612-623.
Clowers, B.H., et al., Pseudorandom Sequence Modification for Ion Mobility Orthogonal Time-of-Flight Mass Spectrometry, Analytical Chemistry, 80, 2008, 2464-2473.
Eiceman, G., et al., Ion mobility spectrometers in national defense, Analytical Chemistry, 76, 2004, 390A-397A.
Fellgett, P., On the ultimate sensitivity and practical performance of radiation detectors, JOSA, 39, 1949, 970-976.
Gao, X., et al., Sources of Negative Peaks in Hadamard Transform/Fourier Transform Mass Spectrometry/Mass Spectrometry, Rapid Communications in Mass Spectrometry, 10, 1996, 1997-2001.
Hirschfeld, T., Fellgett's Advantage in uv-VIS Multiplex Spectroscopy, Applied Spectroscopy, 30, 1976, 68-69.
Ibrahim, Y., et al., Ion Funnel Trap Interface for Orthogonal Time-of-Flight Mass Spectrometry, Analytical Chemistry, 79, 2007, 7845-7852.
International Search Report and Written Opinion for PCT/US2015/016419, dated May 4, 2015, 8 pages.
Kaneta, T., et al., Hadamard Transform Capillary Electrophoresis, Analytical Chemistry, 71, 1999, 5444-5446.
Kwasnik, M., et al., Digitally-Multiplexed Nanoelectrospray Ionization Atmospheric Pressure Drift Tube Ion Mobility Spectrometry, Analytical Chemistry, 81, 2009, 1587-2594.

Office Action from Canadian Patent Application No. 2,942,140, dated Jan. 9, 2017, 4 pages.
Office Action from U.S. Appl. No. 14/197,930 dated Jun. 7, 2017, 16 pages.
Szumlas, A.W., et al., Hadamard Transform Ion Mobility Spectrometry, Analytical Chemistry, 78, 2006, 4474-4481.
Tai, M.H., et al., Errors in Hadamard spectroscopy or imaging caused by imperfect masks, Applied Optics, 14, 11, 1975, 2678-2684.
Zeppenfeld, P., et al., On the origin of spurious peaks in pseudo-random time-of-fight analysis, Review of Scientific Instruments, 64, 1993, 1520-1523.
Office Action from European Patent App. No. 15706659.8 dated Nov. 27, 2018, 5 pages.
Office Action from U.S. Appl. No. 14/197,930 dated Feb. 14, 2018, 16 pages.
Zare et al., "High Speed Mass Spectrometry Hadamard Transform Time-of-Flight Mass Spectrometry: More Signal, More of the Time," Angewandte Chemie Int'l Ed., Jan. 2003, pp. 30-35.
Baker et al., "An LC-IMS-MS Platform Providing Increased Dynamic Range for High-Throughput Proteomic Studies," *Journal of Proteome Research*, Feb. 2011, 7 pages.
Beddard et al., "Pump-Probe Spectroscopy using Hadamard Transforms," *University of Leeds*, Jan. 2011, 10 pages.
Belov et al., "Multiplexed Ion Mobility Spectrometry-Orthogonal Time-of-Flight Mass Spectrometry," *Anal. Chem.*, Mar. 2007, 12 pages.
Brock et al., "Characterization of a Hadamard transform time-of-flight mass spectrometer," *Review of Scientific Instruments*, Mar. 2000, 13 pages.
Brock et al., "Hadamard Transform Time-of-Flight Mass Spectrometry," *Anal. Chem.*, Aug. 20, 1998, 7 pages.
Clowers et al., "Hadamard Transform Ion Mobility Spectrometry," *Anal. Chem.*, vol. 78, No. 1, Jan. 2006, 8 pages.
Decker, "Experimental Realization of the Multiplex Advantage with a Hadamard-Transform Spectrometer," *Applied Optics*, vol. 10, No. 3, Mar. 1971, 5 pages.
Department of Chemistry, Stanford University, "Guide to the Zarelab," Jul. 2010, 23 pages.
Fernandez et al., "Effect of Sequence Length, Sequence Frequency, and Data Acquisition Rate on the Performance of a Hadamard Transform Time-of-Flight Mass Spectrometer," *J. Am. Soc. Mass. Spectrometry*, Dec. 2001, 10 pages.
Fernandez et al., "Hadamard Transform Time-of-Flight Mass Spectrometry: A High-Speed Detector for Capillary-Format Separations," *Anal. Chem.*, Apr. 2002, 7 pages.
Hanley, "Masking, Photobleaching, and Spreading Effects in Hadamard Transform Imaging and Spectroscopy Systems," *Applied Spectroscopy*, vol. 55, Issue 3, 2001, 13 pages.
Harwit et al., *Hadamard Transform Optics*, Chapters 1, 3, 4, and 6, (Bell Telephone Labs, Inc. 1979), 67 pages.
Kimmel et al., "Effects of Modulation Defects on Hadamard Transform Time-of-flight Mass Spectrometry (HT-TOFMS)," *J. Am. Soc. Mass Spectrometry*, Mar. 2003, 9 pages.
Kimmel et al., "Peak Height Precision in Hadamard Transform Time-of-Flight Mass Spectra," *J. Am. Soc. Mass Spectrometry*, Jul. 2005, 14 pages.
MacWilliams and Sloane, "Pseudo-random sequences and arrays," *Proceedings of the IEEE*, vol. 64, Issue 12, Dec. 1976, 15 pages.
Massick, "Final Report: Hadamard Transform Time-of-Flight Mass Spectrometry," AFRL-SR-AR-TR-04-0648, Nov. 2004, 15 pages.
Sloane et al., "Systematic Errors in Hadamard Transform Optics," *Appl. Opt.*, Sep. 1978, 12 pages.
Tang et al., High-Sensitivity Ion Mobility Spectrometry/Mass Spectrometry Using Electrodynamic Ion Funnel Interfaces, *Anal. Chem.*, May 2005, 10 pages.
Thermo Scientific, "Overview of Mass Spectrometry," downloaded from http://www.piercenet.com/browse.cfm?fldID=33C6C4ED-4B0D-49FA-ABD2-23BCB0FADEC0 on Jan. 24, 2013, 5 pages.
Treado et al., "Hadamard Transform Techniques in Photothermal Spectroscopy," *AIP Conference Proceedings*, Oct. 1989, 6 pages.
Wehlburg et al., "High Speed 2D Hadamard Transform Spectral Imager," Feb. 2003, 118 pages.

(56) References Cited

OTHER PUBLICATIONS

Wikipedia, "Hadamard matrix," downloaded from http://en.wikipedia.org/wiki/Hadamard_matrix on Jan. 24, 2013, 6 pages.
Wikipedia, "Hadamard transform," downloaded from http://en.wikipedia.org/wiki/Hadamard_transform on Jan. 24, 2013, 5 pages.
Wikipedia, "Secondary ion mass spectrometry," downloaded from http://en.wikipedia.org/wiki/Secondary_ion_mass_spectrometry on Jan. 24, 2013, 5 pages.
Wikipedia, "Time-of-flight Mass Spectrometry," downloaded from http://en.wikipedia.org/wiki/Tome-of-flight_mass_spectrometry on Jan. 24, 2013, 9 pages.
Yoon et al., "Duty Cycle and Modulation Efficiency of Two-Channel Hadamard Transform Time-of-Flight Mass Spectrometry," *J. Am. Soc. Mass Spectrometry*, Sep. 2005, 14 pages.
Zare et al., "Hadamard Transform Time-of-Flight Mass Spectrometry: More Signal, More of the Time," *Angewandte Chemie Int'l Ed.*, vol. 42, No. 1, Jan. 2003, 6 pages.
Office Action from Canadian Patent Application No. 2,942,140, dated Oct. 22, 2018, 6 pages.
Office Action from European Patent Application No. EP 15 706 659.8, dated Oct. 12, 2018, 4 pages.
Office Action from U.S. Appl. No. 14/197,930 dated Sep. 17, 2018, 13 pages.
Search Report and Written Opinion for SG Application No. 11201607325W, dated Jan. 23, 2018, 10 pages.

\* cited by examiner

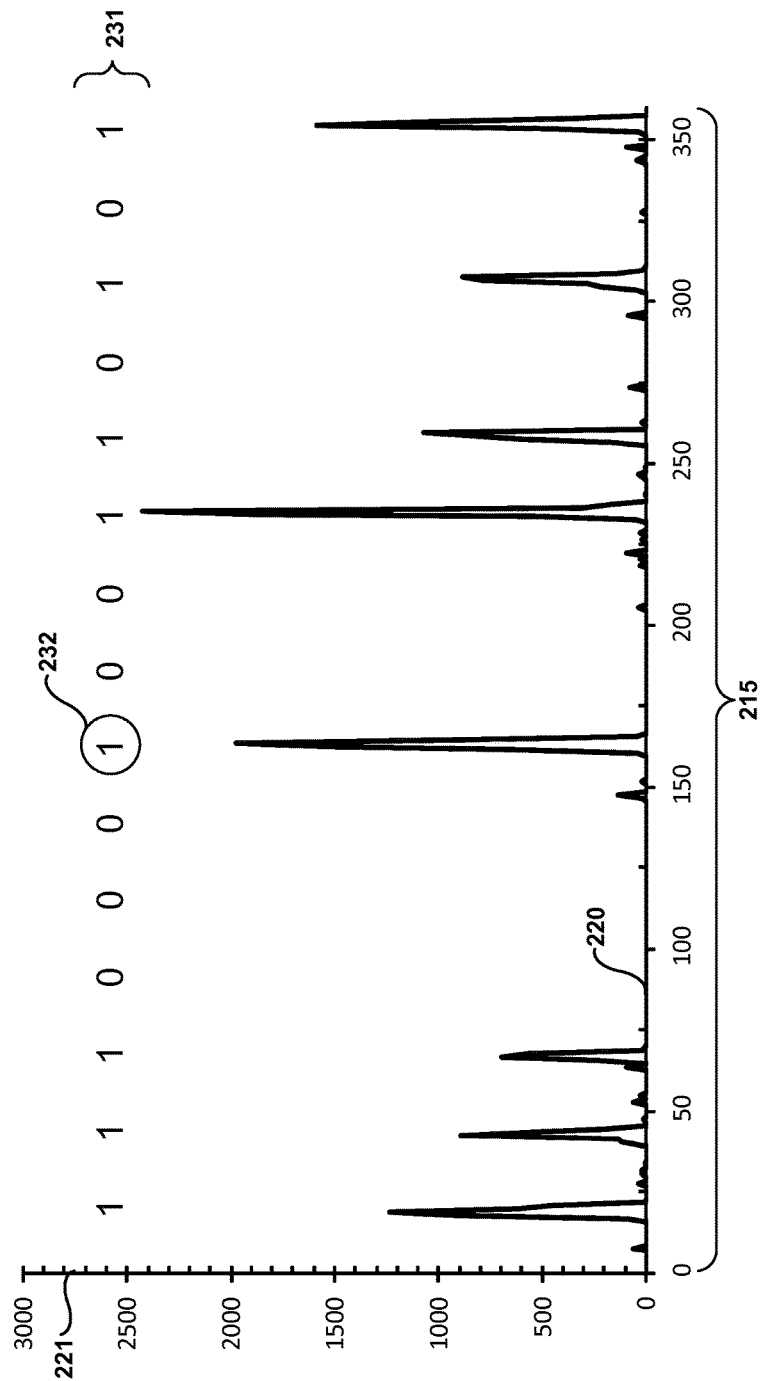

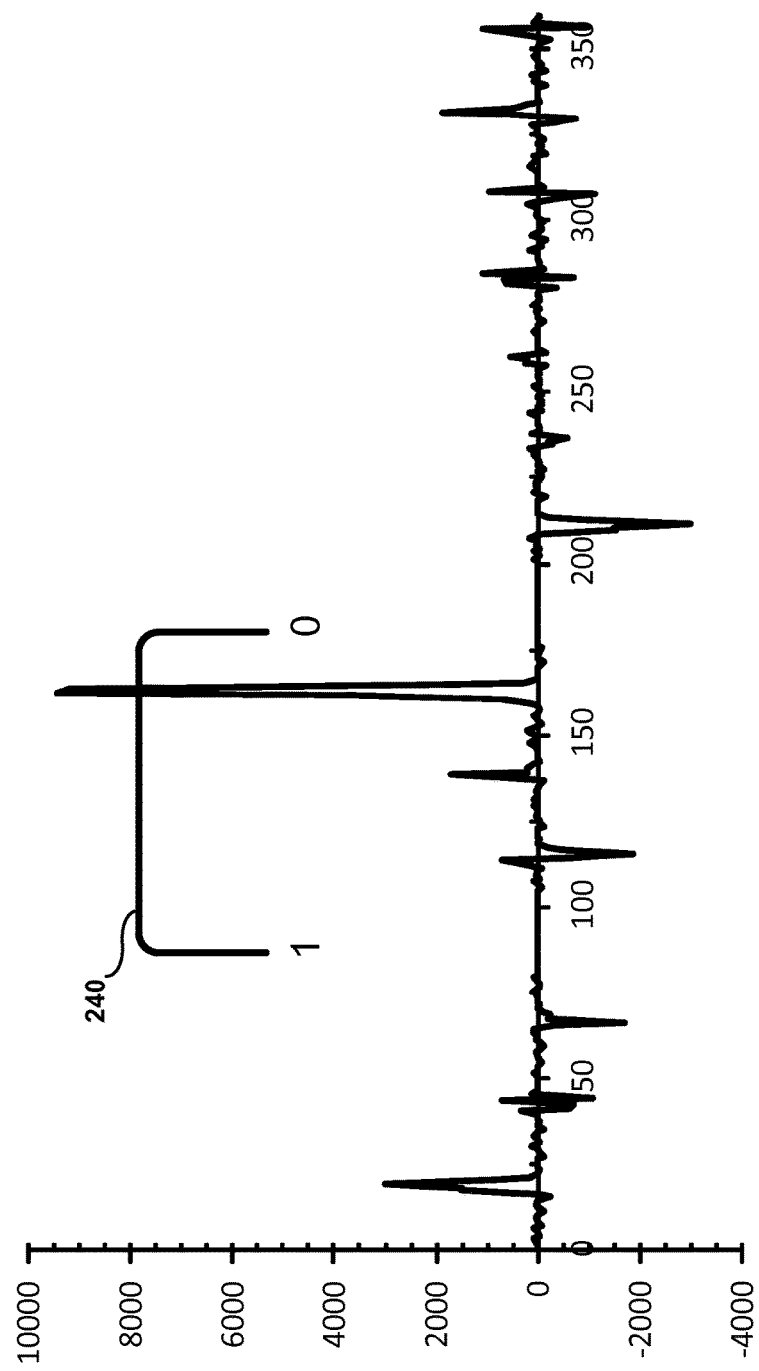

206

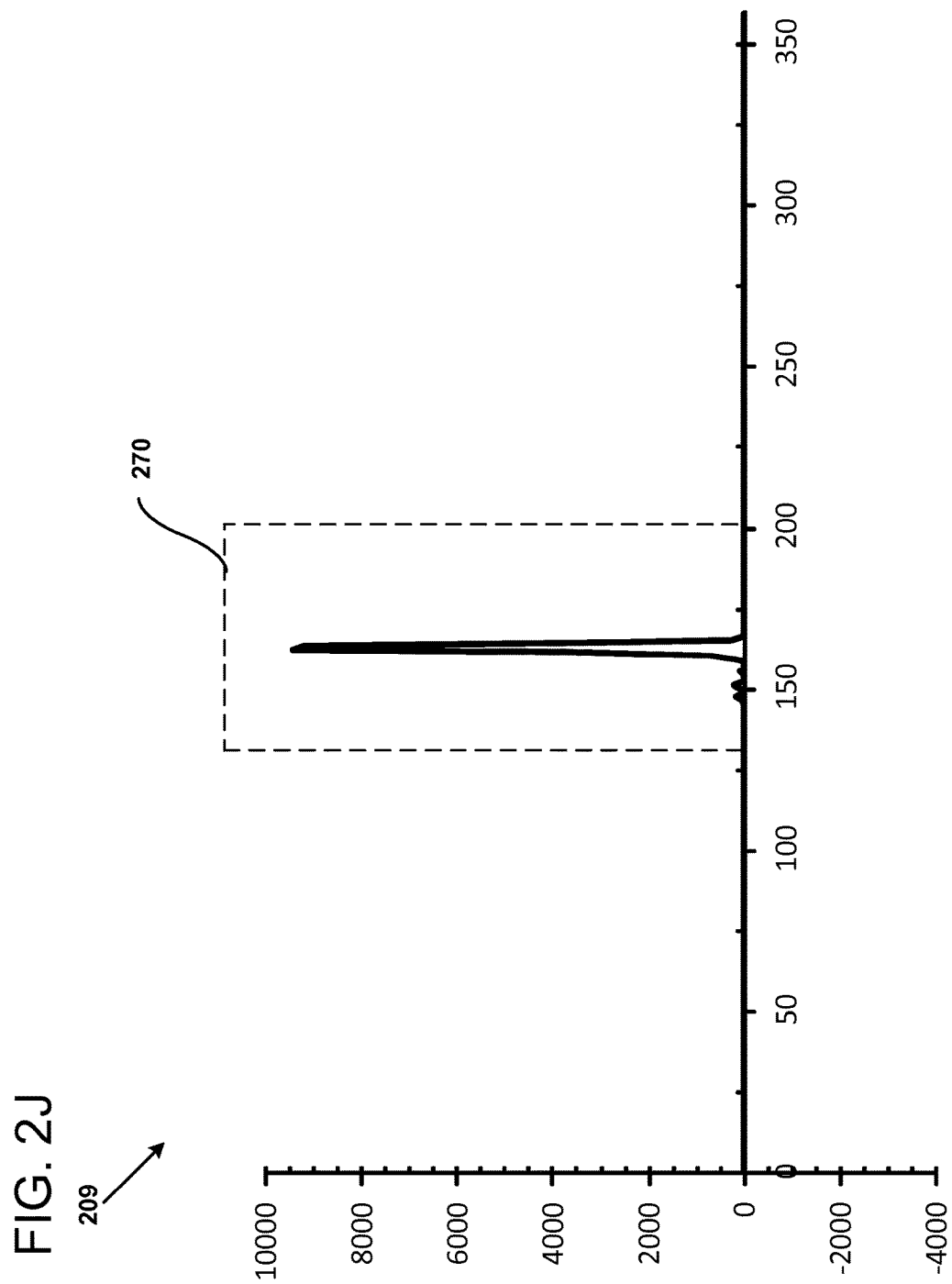

310 — Identify peaks in transformed intensity data

320 — Select an identified peak to validate

330 — Select a PRS bit to compare to untransformed data

PRS bit value?
- No bits remaining to compare
- bit = 0
- bit = 1

Data has peak in untransformed data?
- Yes
- No

350 — Designate peak as valid

340 — Designate and/or remove peak as being invalid

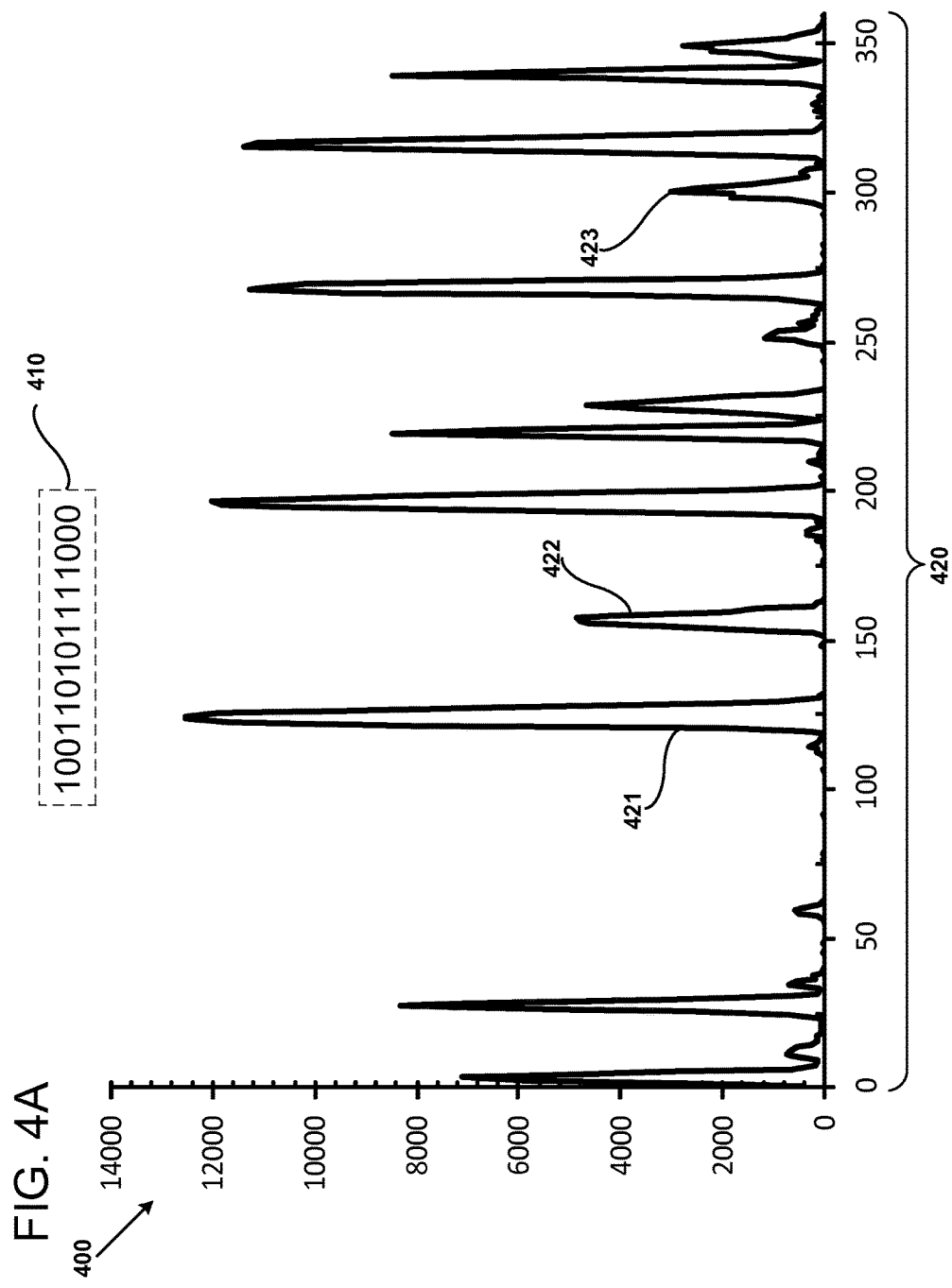

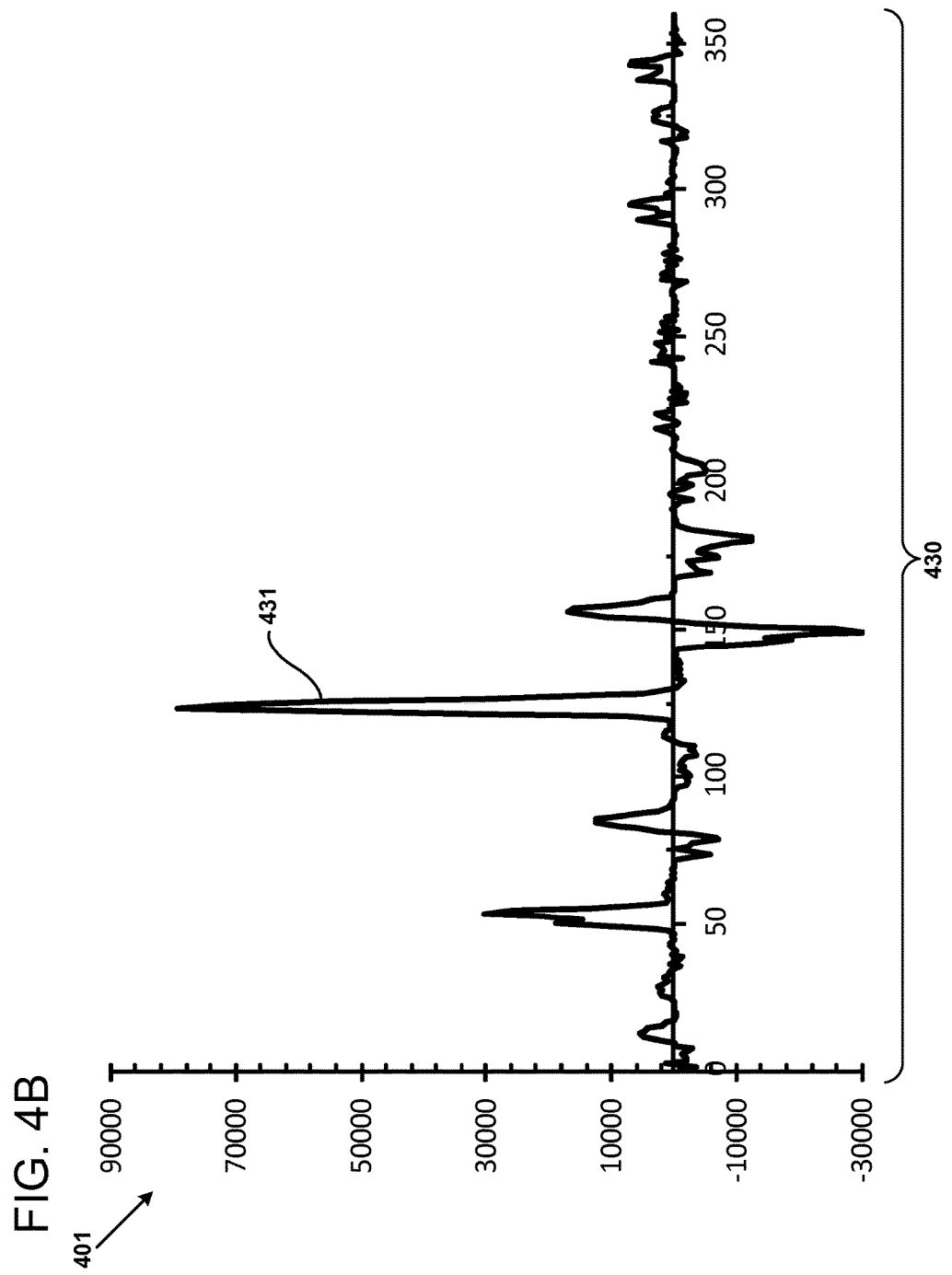

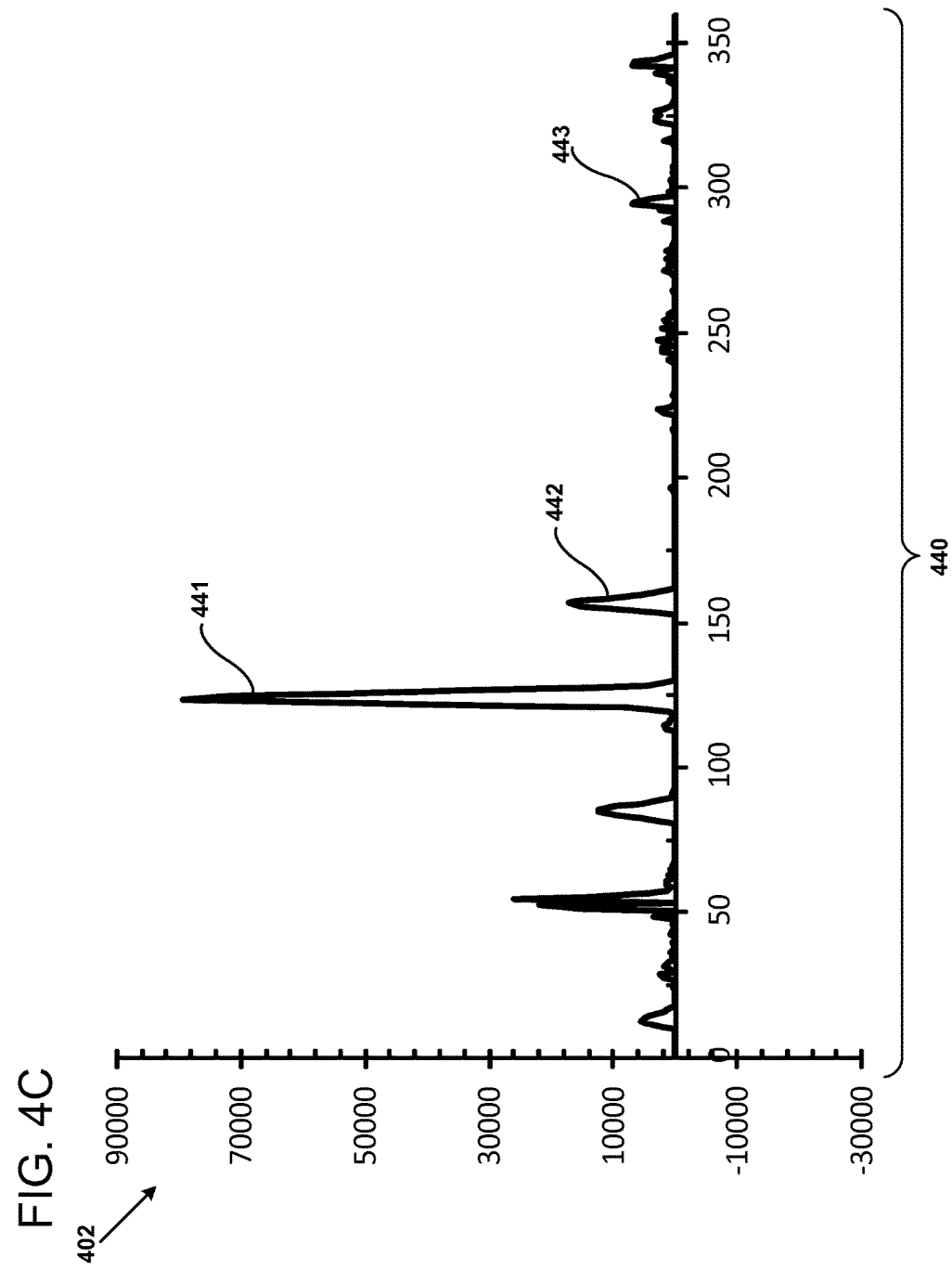

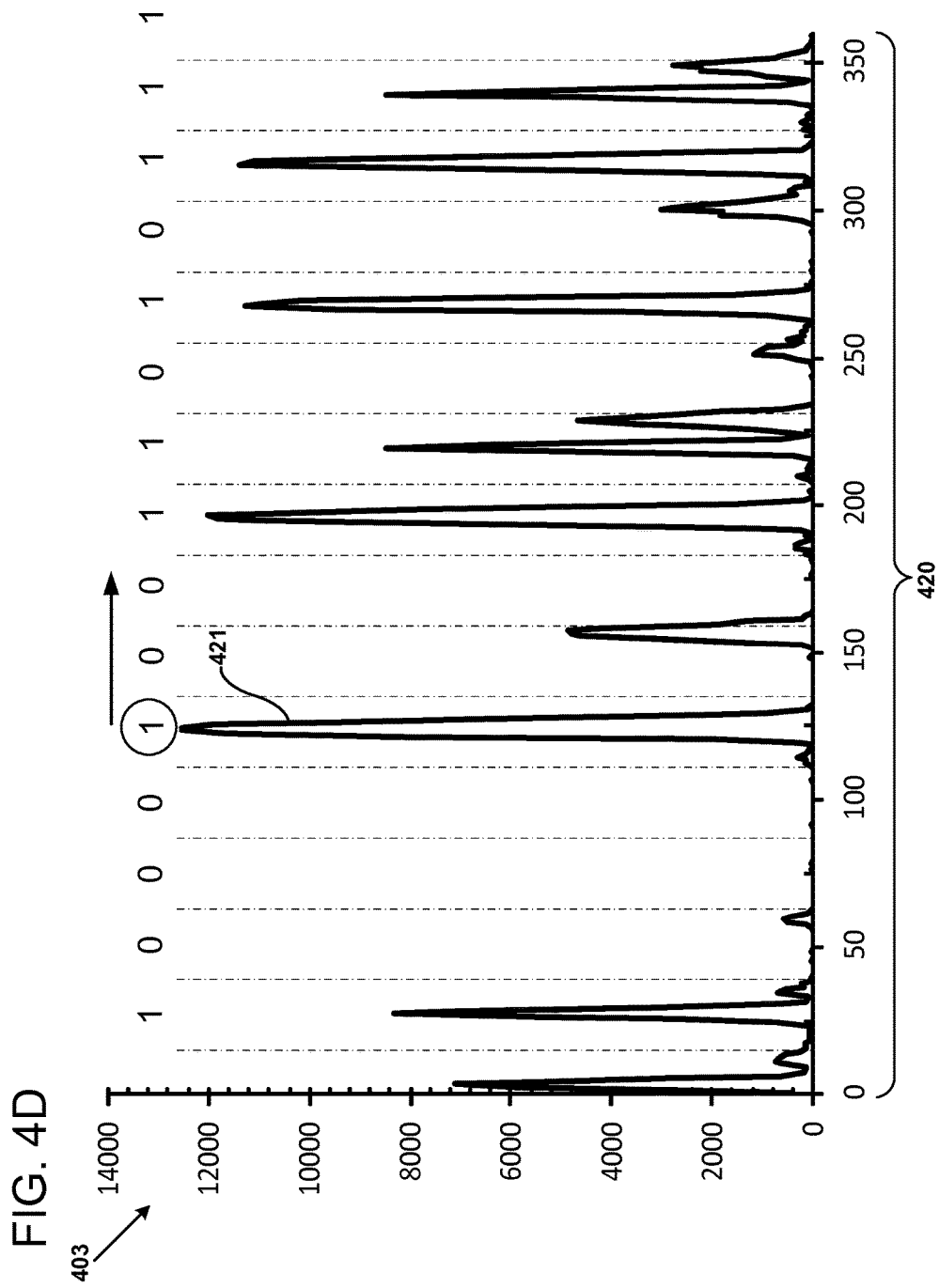

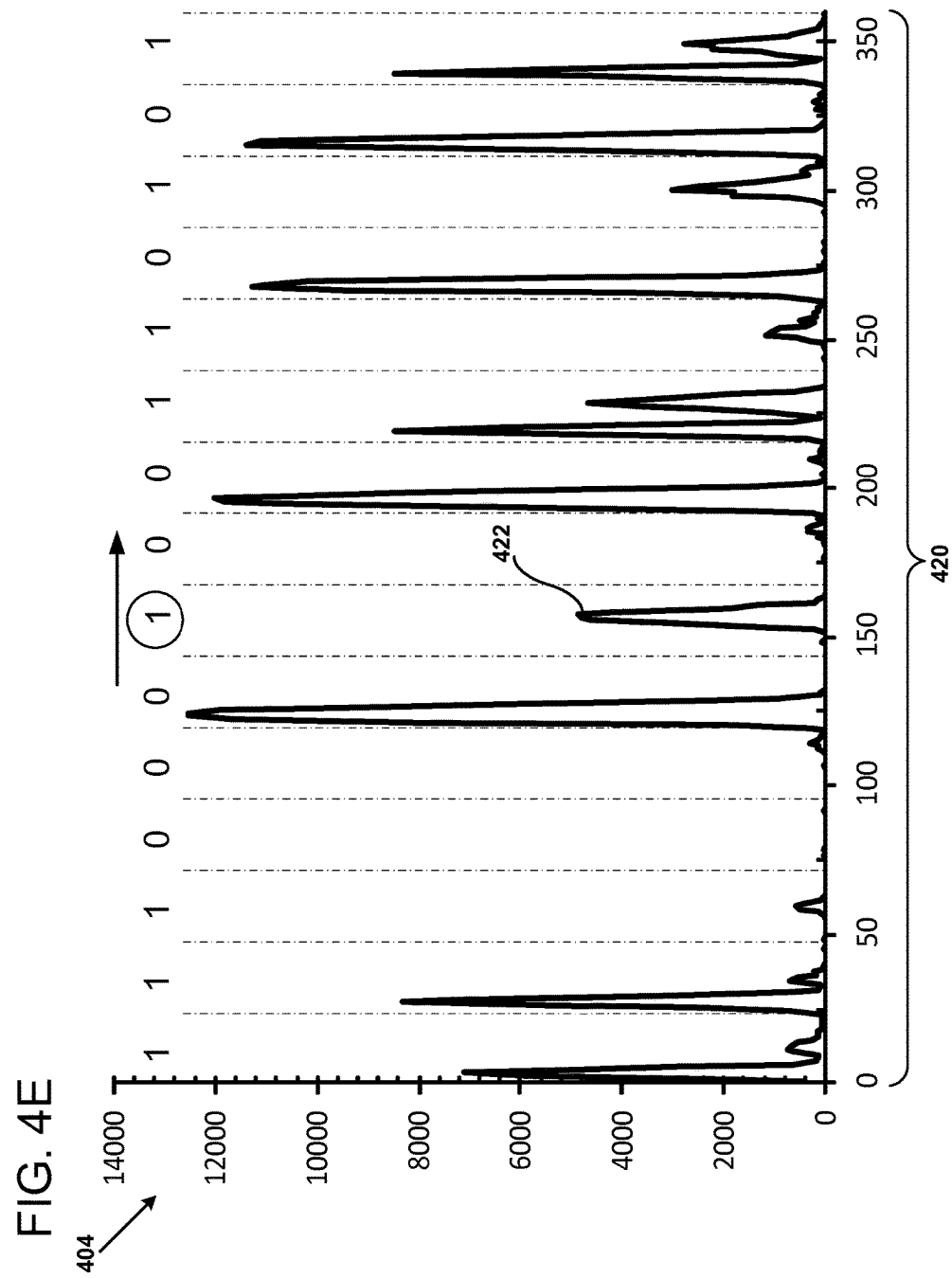

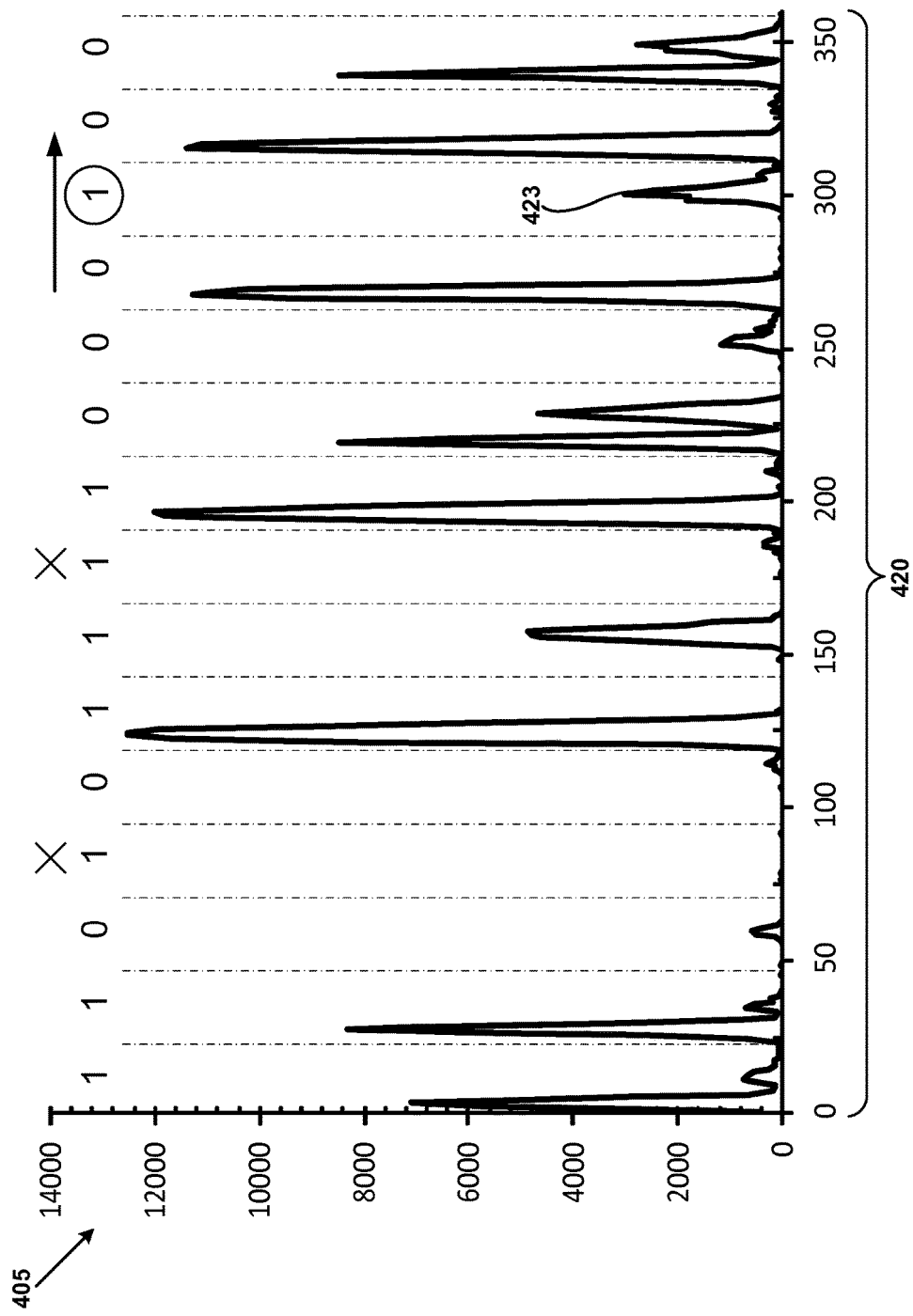

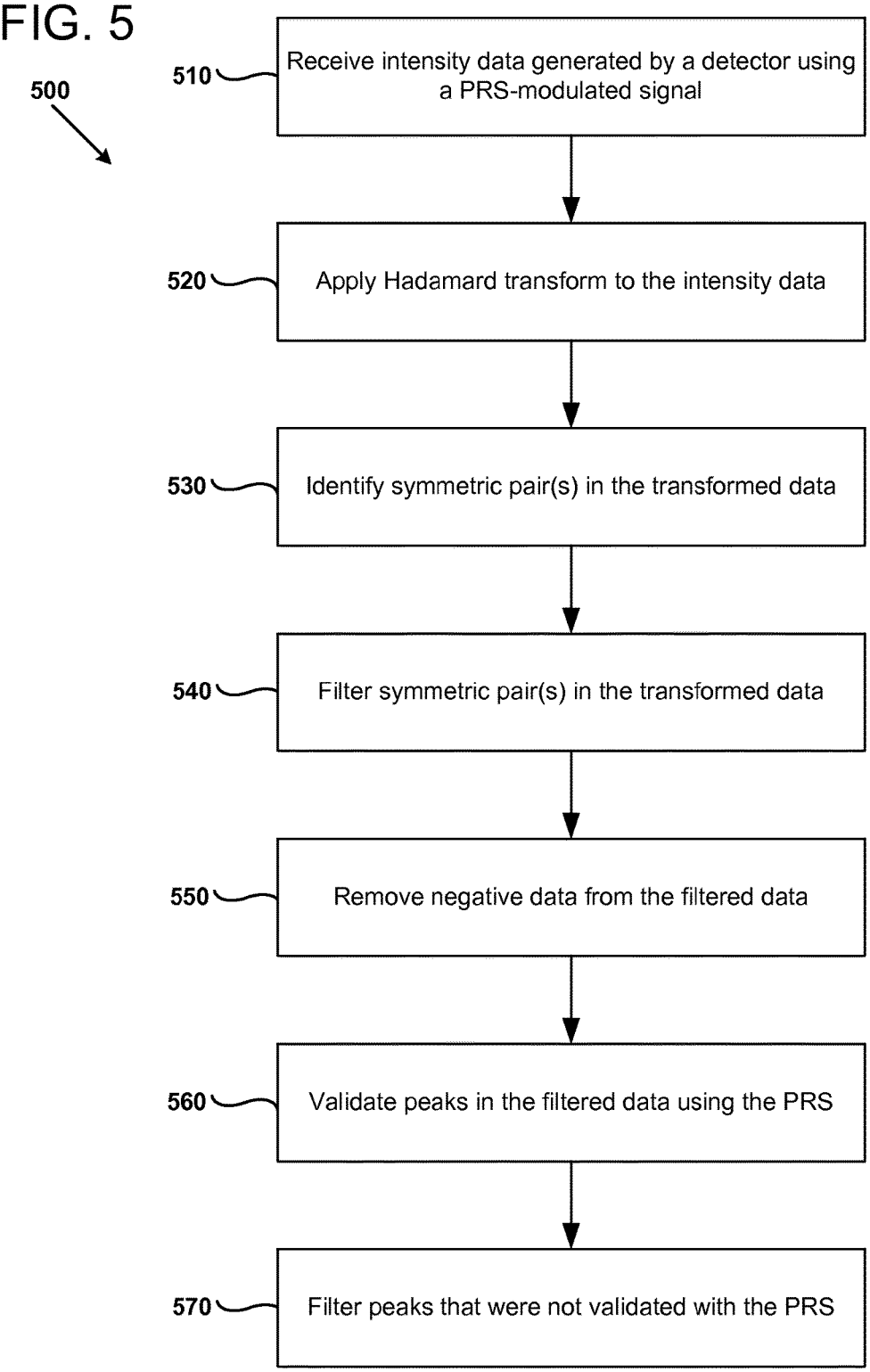

ed data. Some examples of this method
METHODS OF RESOLVING ARTIFACTS IN HADAMARD-TRANSFORMED DATA

CROSS-REFERENCE TO RELATED APPLICATION

This application claims the benefit of U.S. Provisional Application No. 61/800,822, entitled "Hadamard Transform Demultiplexing Process," filed Mar. 15, 2013, and U.S. Provisional Application No. 61/673,320, entitled "Hadamard Transform Demultiplexing Process," filed Jul. 19, 2012, which applications are incorporated by reference herein in their entireties for all purposes.

GOVERNMENT RIGHTS STATEMENT

This invention was made with Government support under contract number DE-AC05-76RL01830 awarded by the U.S. Department of Energy. The Government has certain rights in the invention.

FIELD

The disclosed technology relates to methods and apparatus that can be used with Hadamard-transformed data, including mass spectrometry applications.

BACKGROUND

Hadamard transform multiplexing has been used in mass spectrometry in order to increase the signal-to-noise ratio (SNR) of ion intensity data. When applied to ion mobility mass spectrometry (IMS), the transformed data are susceptible to periodic artifacts, such as those that occur when deconvolution is applied assuming that the data are precisely aligned to the mathematical sequence used to encode it.

Previous techniques, for example, those discussed by Belov et al. in U.S. Pat. No. 7,541,675, involve the use of multiplexing with an ion mobility spectrometry (IMS) quadrupole time-of-flight (QTOF) mass spectrometry instrument, which utilizes an ion trap that allows for higher ion utilization and duty cycles greater than 50%.

SUMMARY

Applying a Hadamard transform multiplexing scheme to an ion mobility mass spectrometer instrument system can improve the signal-to-noise ratio and duty cycle of the instrument. A pseudorandom sequence (or "PRS") is used to both encode and decode the data. However, minor perturbations in the convolved data that do not perfectly align with the pseudorandom sequence will cause periodic "echo" artifacts that lower the signal-to-noise ratio (SNR) and appear as noise in downstream processing of the data (e.g., processing of the deconvolved or transformed data). Certain embodiments disclosed herein include the use of general deterministic numerical analysis to discover and eliminate periodic data artifacts based on knowledge of the deconvolution of the pseudorandom sequence, thereby boosting the SNR. Instruments that utilize simplex matrices and the Hadamard transform can utilize this technique. The decoded data exhibit a type of periodic symmetry about an axis of reflection corresponding to the encoding pseudorandom sequence, which can be utilized to remove the resulting data artifacts. Knowledge of the true signal peaks that is derived from the encoded data allows for both artifacts and noise to be removed with high confidence, decreasing the likelihood of false identifications in subsequent data processing.

In some examples of the disclosed technology, a method of resolving data artifacts in Hadamard transformed data includes identifying at least one pair of symmetric intensity peaks in the Hadamard transformed data using a pseudorandom sequence (PRS) that was used to generate the Hadamard transformed data and filtering the identified pair of symmetric peaks from the transformed data, thereby producing filtered data. Some examples of this method include removing negative data from the filtered data, validating peak(s) in the filtered data, and filtering or removing non-validated peaks from the transformed data. In some examples, for 1 value bits of a PRS corresponding to a portion of time, existence of a peak in untransformed data (on which the transformed data is based) is confirmed; conversely for 0 bits of the PRS, the existence of a peak in the untransformed data is ignored. In some examples, a Hadamard transform is applied to intensity data generated by a detector in response to receiving a signal modulated by the PRS.

In some examples, an apparatus for performing this method includes a spectrometer comprising a gate configured to modulate introduction of analytes to a detector according to the PRS. Logic (e.g., processor(s) and/or reconfigurable logic devices such as FPGAs) coupled to the detector operates the gate, modulating introduction of the analytes to the detector.

In some examples of the disclosed technology, a method of resolving data artifacts in Hadamard transformed data includes validating peaks in transformed data using a pseudorandom sequence (PRS) and filtering the peaks that were not validated. In some examples, if there is a peak in the untransformed intensity data at a portion of the untransformed data corresponding to a 1 bit of the PRS, the selected peak is designated as valid, and if there is not a peak in the untransformed data at first portion corresponding to a 1 bit of the PRS, the selected peak is designated as invalid. In some examples, the selected peak is designated as valid even if there are peaks in the untransformed data at any portion corresponding to a 0 bit of the PRS.

In some examples of the disclosed technology, a method of resolving data artifacts in Hadamard transformed data includes identifying at least one pair of symmetric peaks in the Hadamard transformed data using a pseudorandom sequence (PRS) that was used for producing the Hadamard transformed data, filtering the identified pair of symmetric peaks from the transformed data, removing negative data from the filtered data, validating peaks in the filtered data using the PRS, and filtering the peaks that were not validated with the PRS.

In some examples, one or more computer-readable storage media store computer-readable instructions that when executed by a computer, cause the computer to perform one or more of the foregoing methods. In some of the foregoing examples, the meaning of the 0 bits and 1 bits is swapped (thus, peaks are ignored for 1 bits and validated for 0 bits), and in other examples, different symbols are used to describe the PRS.

This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the invention will become more apparent from the following detailed description, which proceeds with reference to the accompanying figures.

BRIEF DESCRIPTION OF THE DRAWINGS

FIGS. 2A-2J are charts that illustrate data processing in an exemplary implementation of the disclosed technology.

FIG. 3 is a flow chart that outlines an exemplary implementation of validating peaks as can be used in certain embodiments of the disclosed technology.

FIG. 4A-4G are charts that illustrate data processing in an exemplary implementation of the disclosed technology.

FIG. 5 is a flow chart that outlines an exemplary implementation of filtering data as can be used in certain embodiments of the disclosed technology.

DETAILED DESCRIPTION

I. General Considerations

Figure 1:
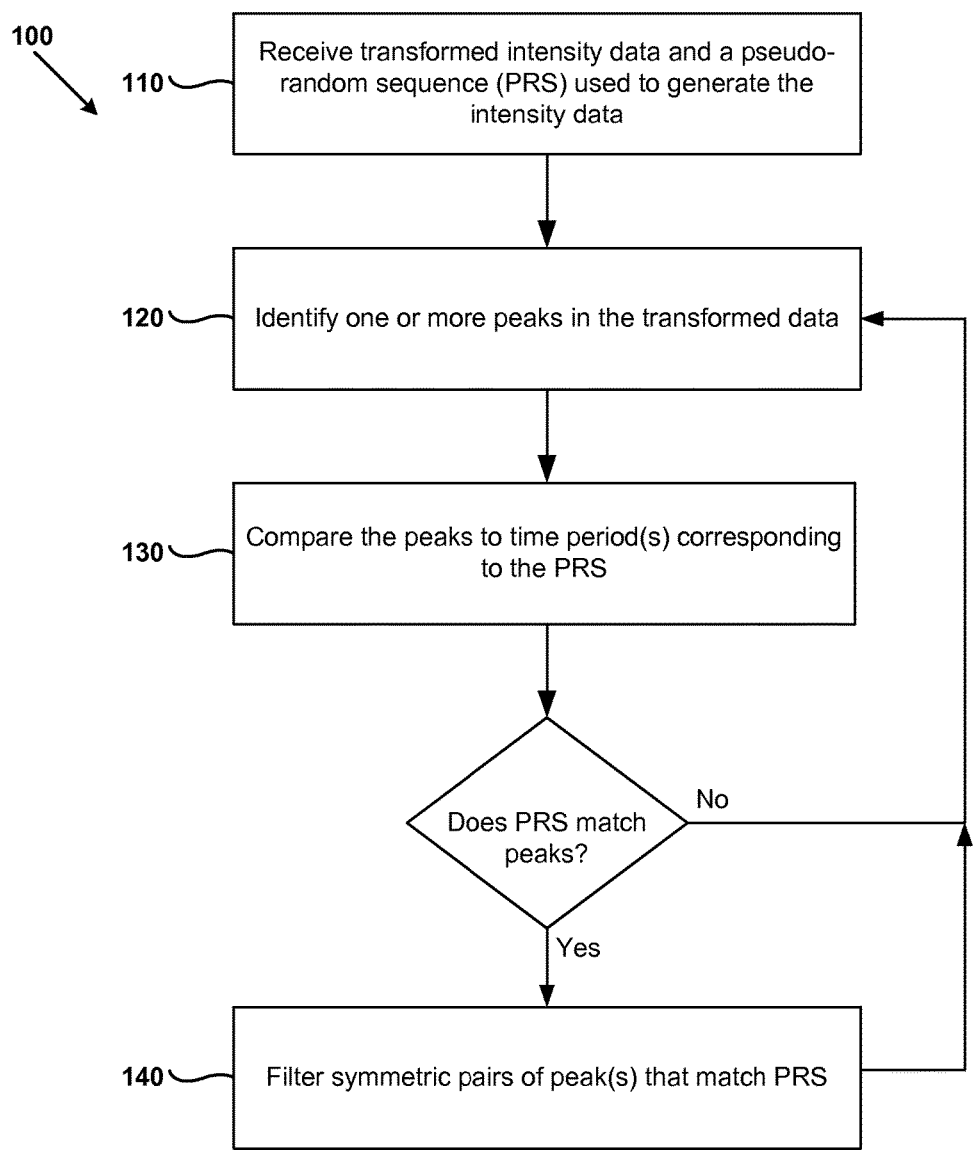
FIG. 1 is a flow chart that outlines an exemplary implementation of filtering symmetric pairs as can be used in certain embodiments of the disclosed technology.

This disclosure is set forth in the context of representative embodiments that are not intended to be limiting in any way.

As used in this application and in the claims, the singular forms "a," "an," and "the" include the plural forms unless the context clearly dictates otherwise. Additionally, the term "includes" means "comprises."

The systems, methods, and apparatus disclosed herein should not be construed as being limiting in any way. Instead, this disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Furthermore, any features or aspects of the disclosed embodiments can be used in various combinations and sub-combinations with one another. Furthermore, as used herein, the term "and/or" means any one item or combination of items in the phrase.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged, omitted, or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "receive," "produce," "identify," "transform," "modulate," "calculate," "predict," "evaluate," "validate," "apply," "determine," "generate," "associate," "select," "search," and "provide" to describe the disclosed methods. These terms are high-level abstractions of the actual operations that are performed. The actual operations that correspond to these terms can vary depending on the particular implementation and are readily discernible by one of ordinary skill in the art.

Some of the disclosed methods can be implemented with computer-executable instructions stored on one or more computer-readable storage media (e.g., non-transitory computer-readable media, such as one or more volatile memory components (such as DRAM or SRAM), or nonvolatile memory components (such as hard drives) and executed on a computer. Any of the computer-executable instructions for implementing the disclosed techniques as well as any data created and used during implementation of the disclosed embodiments can be stored on one or more computer-readable media (e.g., non-transitory computer-readable media). The computer-executable instructions can be part of, for example, a dedicated software application or a software application that is accessed or downloaded via a web browser or other software application (such as a remote computing application). Such software can be executed, for example, on a single local computer (e.g., any suitable commercially-available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well-known in the art are omitted. For example, it should be understood that the disclosed technology is not limited to any specific computer language or program. Likewise, the disclosed technology is not limited to any particular computer or type of hardware. Certain details of suitable computers and hardware are well-known and need not be set forth in detail in this disclosure.

Theories of operation, scientific principles, or other theoretical descriptions presented herein in reference to the systems, methods, and apparatus of this disclosure have been provided for the purposes of better understanding and are not intended to be limiting in scope. The systems, methods, and apparatus in the appended claims are not limited to those systems, methods, and apparatus that function in the manner described by such theories of operation.

II. Introduction to the Disclosed Technology

Matrix transform multiplexing (e.g., Hadamard transform multiplexing) can been used with time-of-flight mass spectrometers to increase the duty cycle and overall resolution of the instrument. In one example using a pulsed ion mobility spectrometry (IMS) separation, the process begins with a discrete packet of ions entering an ion funnel trap via a heated capillary. The ionization of gas or vapor molecules can be performed using photoionization, electrospray, or matrix-assisted laser desorption/ionization, or other suitable technique. The duty cycle of a traditional orthogonal ion mobility spectrometry quadrupole time of flight mass spectrometer (IMS-QTOF-MS) is typically approximately 10% without multiplexing due to a requirement of the instrument that all ions must arrive at the detector before the next packet of ions is pulsed. The duty cycle can vary based on the trap and separation time. Otherwise, a spectral overlap will occur that may prevent adequate identification of individual ions. In order to obtain higher resolution, relatively small packet sizes (relative to the total scan time) are introduced into the drift cell.

The Hadamard matrix $H_m$ is a $2^m \times 2^m$ matrix that (scaled by a normalization factor) can be used to transform $2^m$ real numbers $x_n$ into $2^m$ real numbers $X_k$. The Hadamard transform can be defined recursively or by using a binary (i.e., base-2) representation of the indices n and k.

The 1×1 Hadamard transform $H_0$ can be defined by the identity $H_0=1$. The matrix $H_m$ for m>0 can then be recursively defined by:

$$H_m = \frac{1}{\sqrt{2}}\begin{pmatrix} H_{m-1} & H_{m-1} \\ H_{m-1} & -H_{m-1} \end{pmatrix}$$

where $$\frac{1}{\sqrt{2}}$$

is a normalization factor that is sometimes omitted. Thus, other than this normalization factor, Hadamard matrices are made up entirely of 1 and −1.

The Hadamard matrix can also be defined using a binary representation by defining the (k, n)-th entry of the matrix as follows:

$$k = \sum_{0}^{i<m} k_i 2^i = k_{m-1}2^{m-1} + k_{m-2}2^{m-2} + \ldots + k_1 2 + k_0$$

and $$n = \sum_{0}^{i<m} n_i 2^i = n_{m-1}2^{m-1} + n_{m-2}2^{m-2} + \ldots + n_1 2 + n_0$$

where the $k_j$ and $n_j$ are the binary digits (0 or 1) of k and n, respectively. Note that for the element in the top left corner of the matrix, the definition k=n=0 is defined. In this case, we have:

$$(H_m)_{k,n} = \frac{1}{2^{\frac{m}{2}}}(-1)^{\sum_j k_j n_j}$$

Some examples of Hadamard matrices follow.

$$H_0 = +1$$

$$H_1 = \frac{1}{\sqrt{2}}\begin{pmatrix} 1 & 1 \\ 1 & -1 \end{pmatrix}$$

$$H_2 = \frac{1}{2}\begin{pmatrix} 1 & 1 & 1 & 1 \\ 1 & -1 & 1 & -1 \\ 1 & 1 & -1 & -1 \\ 1 & -1 & -1 & 1 \end{pmatrix}$$

-continued $$H_3 = \frac{1}{2^{\frac{3}{2}}}\begin{pmatrix} 1 & 1 & 1 & 1 & 1 & 1 & 1 & 1 \\ 1 & -1 & 1 & -1 & 1 & -1 & 1 & -1 \\ 1 & 1 & -1 & -1 & 1 & 1 & -1 & -1 \\ 1 & -1 & -1 & 1 & 1 & -1 & -1 & 1 \\ 1 & 1 & 1 & 1 & -1 & -1 & -1 & -1 \\ 1 & -1 & 1 & -1 & -1 & 1 & -1 & 1 \\ 1 & 1 & -1 & -1 & -1 & -1 & 1 & 1 \\ 1 & -1 & -1 & 1 & -1 & 1 & 1 & -1 \end{pmatrix}$$

$$(H_n)_{i,j} = \frac{1}{2^{\frac{n}{2}}}(-1)^{i \cdot j}$$

where i·j is the bitwise dot product of the binary representations of the numbers i and j. For example, if n≥2, then $(H_n)_{3,2}=(-1)^{3\cdot 2}=(-1)^{(1,1)\cdot(1,0)}=(-1)^{1+0}=(-1)^1=-1$, agreeing with the above (ignoring the overall constant). Note that the first row, first column of the matrix is denoted by $(H_n)_{0,0}$.

Hadamard transform ion mobility spectrometry (IMS) time-of-flight mass spectrometry can increase the duty cycle to greater than 50%. For example, using a 4 ms trapping time and releasing 8 packets during a 60 ms separation time would result in a duty cycle of $32/60$, or 53%. When using IMS, several ion packets are simultaneously traveling in the flight tube. The packets are encoded by modulating transmission of the ion beam based on a Hadamard matrix generated by a pseudorandom sequence. Due to overlap in ions, the data are convolved using a simplex matrix (or S-matrix), which is based on "1"s and "0"s of the pseudorandom sequence representing the gating of the ions. Based on the encoding scheme, the data are deconvoluted, resulting in a substantial signal-to-noise ratio (SNR) improvement.

Noise and artifacts both tend to distort the deconvolved data. Noise is statistically distributed (and tends towards a Gaussian distribution), whereas artifacts are usually introduced due to a pseudorandom sequence that does not accurately match the on and off states of the pulsed ion source. This causes the simplex matrix, $S_n$, which is based on the pseudorandom sequence, to convolve the data in a way that produces artifacts or defects.

Filtering can be performed by treating remaining data for a portion of the overall time-of-flight period (or a "time segment bin") as noise and eliminating the data without considering whether the data represent real signal values. However, using such cutoff regions in the ion mobility space actually eliminates real data, especially +1 charge state ions, which tend to drift for higher m/z (mass-to-charge) ratios.

Therefore, technologies based on identifying data artifacts that are a result of applying an invertible transform (e.g., a Hadamard Transform) to received intensity data can be used to eliminate both data artifacts and noise while real data are maintained. Knowledge of the bit sequence and periodicity can be used to eliminate data artifacts. Deconvolved data remaining in transformed data after applying a Hadamard Transform corresponds to the pseudorandom bit sequence used in generating the intensity data. Positive and negative peaks display periodicity with a period of a time in which analytes are introduced into a spectrometer. By introducing (or not introducing) analytes into the spectrometer at regular intervals according to a pseudo-random sequence, subsequent analysis of the intensity data using time segment bins having a duration based on the length of these intervals, can assist in analysis of the intensity data. It should be noted that the location of time segment bins can vary based on, for example, the sample and drift cell used.

Intensity values of the deconvolved data often have corresponding reflected values. These values indicate a periodicity of the data corresponding to the bit sequence. These data points tend to exhibit symmetry about an axis of reflection. True peaks will not display periodicity or have a symmetric pair. Symmetric pairs are identified pairs of peaks in data that have symmetrical characteristics. For example, a pair of peaks may exhibit symmetry about the x-axis. Such symmetric pairs can be introduced when a Hadamard transform is applied to intensity data, and are an undesirable artifact of applying the transform. After removing symmetric pairs of peaks, the amount and locations of "true" peaks can be determined by examining the encoded data and comparing to the bit sequence used for the multiplexing process.

Some of the technologies disclosed herein are based on a discovery that points in post-Hadamard transformed data are symmetric about an axis of reflection. Some of the technologies use a priori knowledge of the bit sequence, periodicity, and/or symmetry to eliminate data artifacts in transformed data. Some of the technologies use an identification of the number of real peaks that should appear in the decoded data by examining the nature of the encoded data prior to demultiplexing.

Some of the technologies disclosed herein can be applied to any signal data or instrument that uses a Hadamard transform. Such embodiments can efficiently remove artifacts and noise, while retaining real data, such as Hadamard transform IMS-QTOF-MS (Ion Mobility Spectrometry-Quadrupole Time of Flight-Mass Spectrometry) data.

III. Exemplary Method of Filtering Data by Removing Symmetric Pairs

FIG. 1 is a flow chart 100 that outlines an exemplary method of filtering transformed data by identifying and removing one or more pairs of symmetric peaks, as can be used in certain examples of the disclosed technology. Although the method of FIG. 1 is described using an example of processing analyte intensity data received with a spectrometer, the disclosed techniques can be used to process any other suitable data that has been produced with an invertible transform (e.g., a Hadamard transform), as will be readily apparent to one of ordinary skill in the art.

At process block 110, transformed intensity data and a pseudorandom sequence (PRS) used to generate the transformed intensity data are received (e.g., with an I/O interface or network interface of a suitable computing environment).

In some examples, the transformed intensity data, which is based on applying a transform to encoded (untransformed) data, can be expressed in terms of ion counts received at a number of different times or during a number of different time segments. In some examples, the transformed intensity data is generated when a number of analytes are received at a detector based on a pseudorandom sequence. Analytes can be introduced into an ion mobility mass spectrometer according to a gating sequence applied based on the pseudorandom sequence. For example, when the pseudorandom sequence includes a 1, analytes are allowed to enter the spectrometer for the corresponding time segments. On the other hand, if the pseudorandom sequence includes a 0, analytes are not allowed to enter the spectrometer for the corresponding time segments. As will be readily understood by those of ordinary skill in the art, the assignment of 1's to opening the gate and 0's to closing the gate according to the pseudorandom sequence is arbitrary, and other suitable conventions can be used to describe the sequence.

Shifts in the location of the multiplexed peaks (e.g., approximately ¼ to ½ of a scan) generate periodic echo peaks that are symmetric about an axis. The periodicity of the data is a type of artifact error which is distinct from noise in that it does not exhibit tendencies to conform to the central limit theorem, and does not resemble any known distribution. Two points are symmetric about an axis of reflection and are the same value except for one being (potentially) the negation of the other. The axis may be, but is not limited to, y=0 in general, but the axis of reflection can theoretically occur anywhere in the range (−∞, ∞). This axis of reflection interval implies that two values may both be positive, or negative, yet still be reflected about an axis, and therefore be symmetric. The processing of the Hadamard transformed data can utilize translation of the scan intensity values to reflect about an axis, such as y=0.

After receiving the transformed intensity data and the PRS, the method proceeds to process block 120.

At process block 120, one or more peaks in the transformed data are identified. The peaks may be positive or negative, and can be identified using any suitable technique. For example, absolute values, relative values, thresholds, or shape can be used to identify the one or more peaks. In some examples, the highest intensity peak is also specially indicated versus the other peaks, for use in identifying symmetric pairs. After identifying the peaks, the method proceeds to process block 130.

At process block 130, pairs of symmetric peaks are identified in the transformed data. In some examples, knowledge of the pseudorandom sequence that was applied when generating and receiving the analytes at process block 110 can be used to identify symmetric pairs in the transformed data. For example, the pseudorandom sequence can be reversed and aligned with the highest intensity peak identified at process block 120 to identify symmetric pairs. In some examples, a symmetric pair in the transformed data can be identified based on symmetry of the pairs. For example, peaks of a symmetric pair can be substantially identical across the x-axis (i.e., y=0).

In some examples, the symmetric pairs can be compared to the pseudorandom sequence as follows. If the location of a potential symmetric pair corresponds to two "1"s in the pseudorandom sequence, or two "0"s in the pseudorandom sequence, then the alignment of the pseudorandom sequence to the transformed data is discarded, because the PRS does not properly align with the symmetric pairs Conversely, if for each of the symmetric pairs in the transformed data, one of the peaks in the symmetric pair corresponds to a 1 bit in the PRS, and the other respective peak of the prospective pair corresponds to a 0 bit in the PRS, then the pseudorandom sequence is determined to be aligned to the transformed data according to a shift that matches the symmetric pairs. If a potential pair of symmetric pairs does not match complementary values in the PRS, then the method proceeds back to process block 120 to identify additional pairs of symmetric peaks in the data. Once one or more symmetric pairs have been identified in the transformed data, the method proceeds to process block 140.

At process block 140, filtered data are produced by filtering the transformed data based on the pseudorandom sequence and the peaks identified at process block 120. For example, data associated with a symmetric pair that were identified at process block 140 are removed to produce modified data. Thus, based on knowledge of the pseudorandom sequence that was applied when introducing analytes into the spectrometer, symmetric peaks corresponding to the pseudorandom sequence can be identified and filtered from the data, thereby producing filtered data. In some examples, the method returns to process block 120 to identify additional peaks to be filtered.

In some examples of the disclosed technology, in order to compare two values about the y=0 axis, the values of one of the peaks are inverted and then compared to another peak by taking the difference and determining if that is less than a certain value or margin of error, (e.g., less than an upper bound on relative error due to floating-point rounding, or machine epsilon). If the values are equal within the margin of error, they are determined to be artifacts and set to 0. In this way, periodic data that is symmetric about the axis is eliminated, but real data (e.g., data which does not have a reflected pair about an axis), is preserved. The filtering of periodic data and preservation of real data allows for an improvement to the signal-to-noise ratio (SNR).

After filtering the symmetric pairs, the filtered data produced at process block 140 can then be subjected to further analysis in order to more accurately identify and characterize the composition of the sample used to produce the transformed intensity data at process block 110. This filtered (or modified) data can be used to evaluate the sample that was used to produce the analytes they were by the spectrometer.

Thus in some examples, using knowledge of the PRS used to "encode" the analytes, ion mobility scan intensity values are selectively compared to "periods" that correspond to a matching of "0s" to "1s" in the PRS. A data point can be determined to be "real" (a valid signal data point) based on only two comparisons. These real data points are kept, while data corresponding to data artifacts are removed (e.g., by changing the corresponding filtered data values to 0).

IV. Experimental Results for Filtering Symmetric Pairs from Transformed Data FIGS. 2A through 2J are charts 200-209 depicting an experimental data set as data is transformed and symmetric pairs are filtered. For example, the method illustrated in FIG. 1 can be used to filter the symmetric pairs. Each of the charts 200-209 corresponds to an additional act of data processing as can be performed in identifying peaks of "real" data (for example, transforming the data according to a Hadamard transform or applying a pseudorandom sequence to the transformed data to identify symmetric peaks in the transformed data, and then removing the identified symmetric peaks from the transformed data).

FIG. 2A is a chart 200 illustrating intensity data 215 (e.g., a count of the number of ions detected for a segment of time) plotted along a drift time axis 220 (as shown, the x-axis) expressed in millisecond units. The drift time axis 220 has been divided into 360 time period bins, each of 167 µs (microsecond) duration. The detected intensities corresponding to a drift time are plotted along the y-axis 221. FIG. 2A illustrates an encoding bit sequence 100110101111000 (reference number 230), which was used to control gating of analytes that were generated from a sample into a drift cell and then into a TOF mass spectrometer. The encoding bit sequence 230 is a pseudorandom sequence. In this particular example, the total time period of a drift time sequence corresponds to 360 time units and is shown along the x-axis.

As shown in FIG. 2A, each of the bits of the pseudorandom sequence are aligned to a portion of the drift time period. Because the pseudorandom sequence used included 15 bits, the time period is divided into 15 time segments. Each of the time segments corresponds to a distinct 24-scan period of time in which analytes are (or are not, according to the pseudorandom sequence) introduced into a spectrometer. Note that the superimposed pseudorandom (231) sequence of FIG. 2A is shifted relative to the applied encoding bit sequence 230. The first superimposed 1-bit is circled 232. The shifting is observed because data that are received at the detector were shifted due to delays in analytes traveling from the ion gate to the detector. This drift is not constant, but is dependent upon factors such as the sample being analyzed and the instruments employed. Thus, one aspect of the disclosed technology is determining the proper shift to align bits of the pseudorandom sequence to time segment bins for the transformed data.

It should be noted that the data shown in FIGS. 2A-2J represent a single example, and that in other examples, the number of time units and length of the time segments can be varied according to a number of different parameters, such as the instrument used to generate the data, the number of scans performed, and the length of the pseudorandom sequence.

Figure 2B:
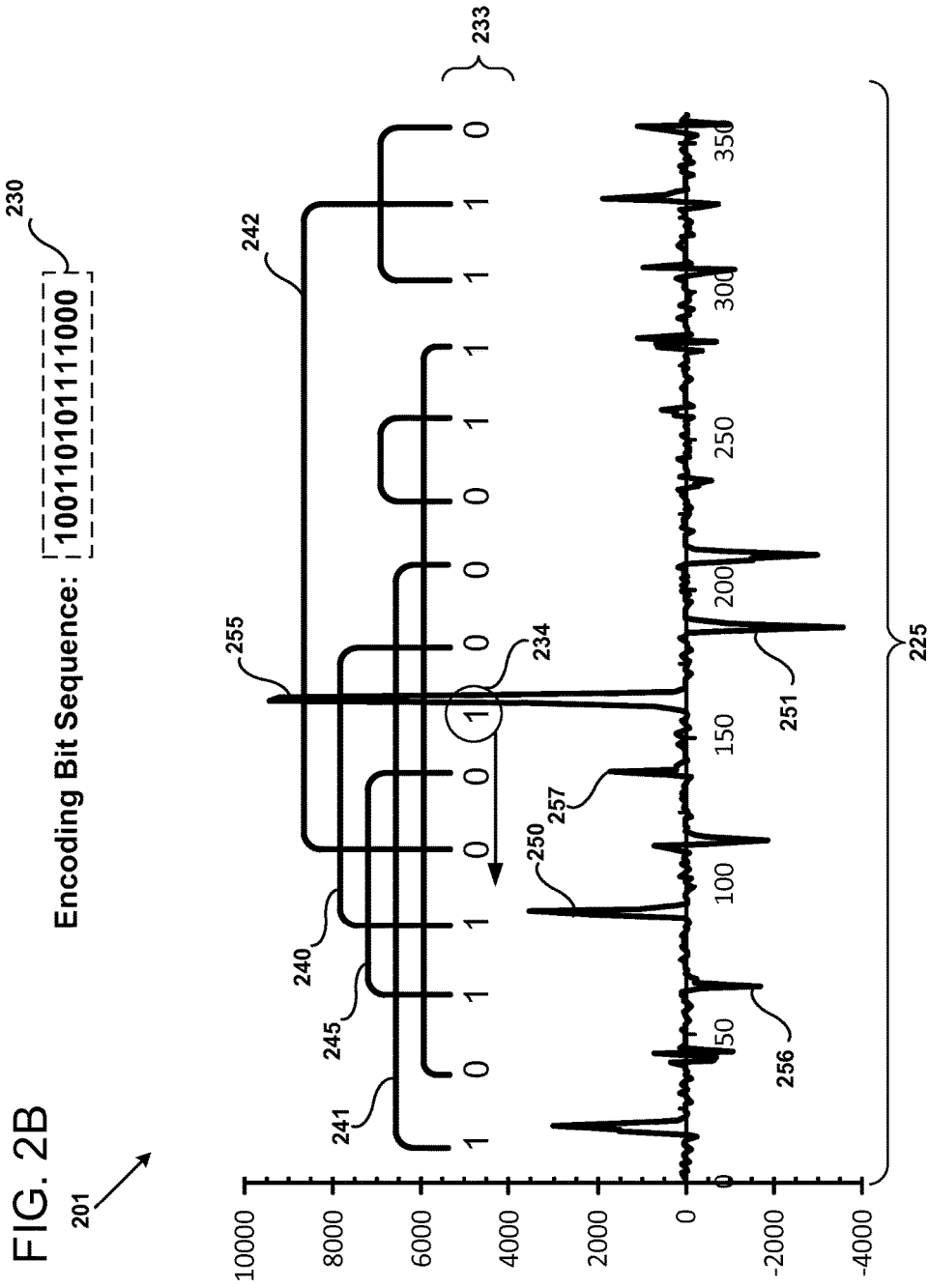

FIG. 2B is a chart 201 illustrating transformed intensity data 225 generated by applying a Hadamard transform to the intensity data 215 shown in FIG. 2A. As shown in FIG. 2B, seven pairs of symmetric peaks (e.g., pairs 240, 241, and 242) are identified in the transformed intensity data 225. In the example of FIGS. 2A-2J, each symmetric pair of intensity values includes a corresponding reflected value, which is usually a negation or opposite of the corresponding peak of the pair, but this property is not necessarily exhibited in other examples. In some examples, true signals in the received data will not display any periodicity or have a symmetric pair.

Each of the seven pairs has a peak associated with a time segment for a value of the PRS (e.g., a "1") and a complementary time segment for a complementary value (e.g., a "0"). For example, FIG. 2B illustrates that the transformed intensity data 225 include a first pair 240, a second pair 241, and a third pair 242 of symmetric peaks. Each of the identified pairs of FIG. 2B have peaks symmetric about the x-axis. For example, symmetric pair 240 includes a first peak 250, and a second peak 251 symmetric to the first peak about the x-axis. Also shown in FIG. 2B is a peak 255 that is not associated with any symmetric pair. The 1-bit associated with this peak 255 is circled in FIG. 2B. As will be discussed further below, this peak represents real signal data and will not be filtered out, as it can be used to evaluate the composition of a sample being analyzed. As used herein, the term "evaluate" refers to analysis including, but not limited to, identification, characterization, and/or quantification of one or more properties of the sample being analyzed and/or its corresponding analytes. For example, molecules of a sample and/or analytes generated from a sample can be identified or quantified.

An example of such an alignment of the PRS to symmetric pairs is illustrated in FIG. 2B. A circle 234 indicates the first bit of the reversed encoding bit sequence 233, which is aligned with the peak 255. The reversed encoding bit sequence 233 is aligned with peaks in the transformed intensity data 225 in the x-direction in the reverse of the order of the encoding bit sequence 230 that was shown in FIG. 2A (in the direction indicated by the arrow). Thus, the second, third, fourth, etc. bits of the encoding bit sequence 230 are aligned with peaks to the left of the starting peak 255. As shown in FIG. 2B, the symmetric pair 240 includes peaks corresponding to the 4th and 15th bit of the pseudorandom sequence 230, while pair 241 includes peaks corresponding to the 7th and 14th bit of the pseudorandom sequence. In some examples, the symmetric pairs will always be located in the same relative location along the drift time axis 220.

It should be noted that the polarity of the peaks does not necessarily correspond to whether the associated bits are a 1 bit or 0 bit. For example, while the pair 240 has a positive peak 250 corresponding to a 1 bit and a negative peak 251 corresponding to a 0 bit, another pair (245) has a negative peak 256 associated with a 1 bit and a positive peak 257 associated with a 0 bit.

The transformed intensity data 225 shown in FIG. 2B have been generated by applying a Hadamard transform to the intensity data 215 of FIG. 2A, by techniques that will be readily apparent to one of ordinary skill in the relevant art. However, other invertible transforms besides the Hadamard transform may be used.

Figure 2D:
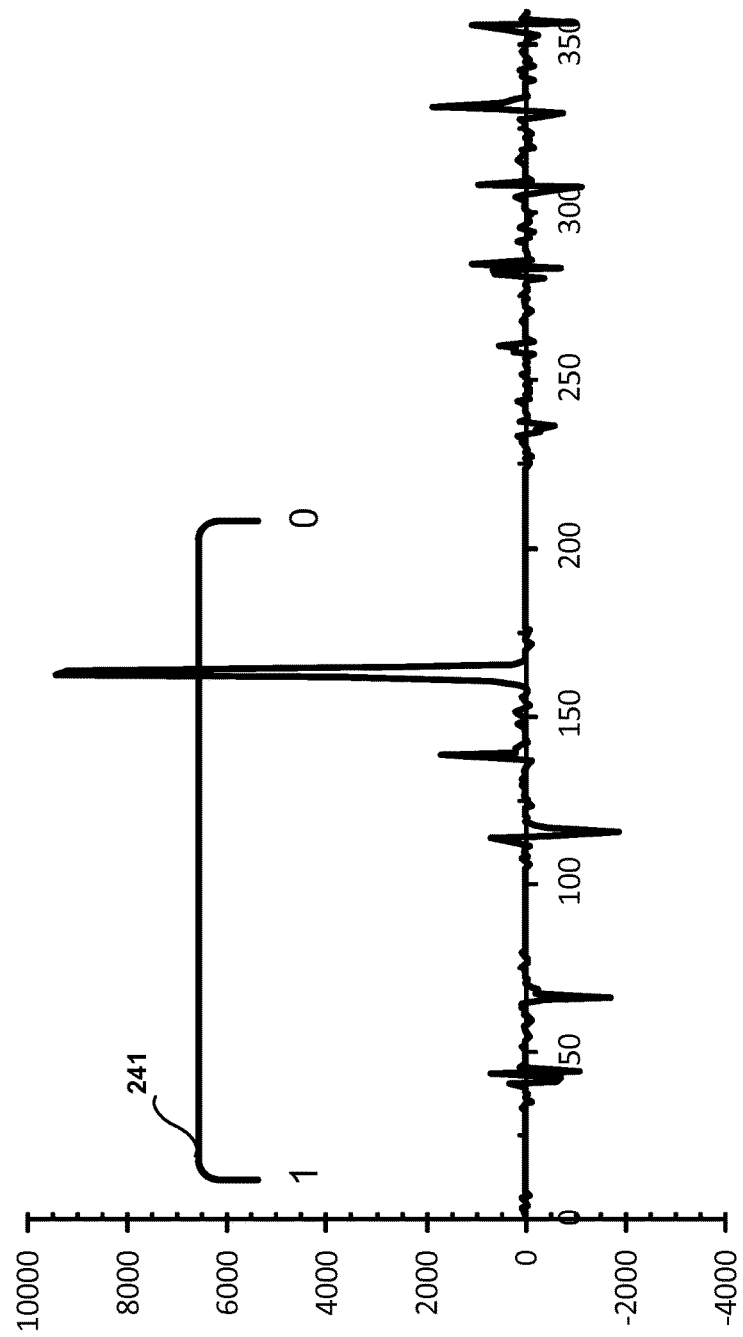
Figure 2E:
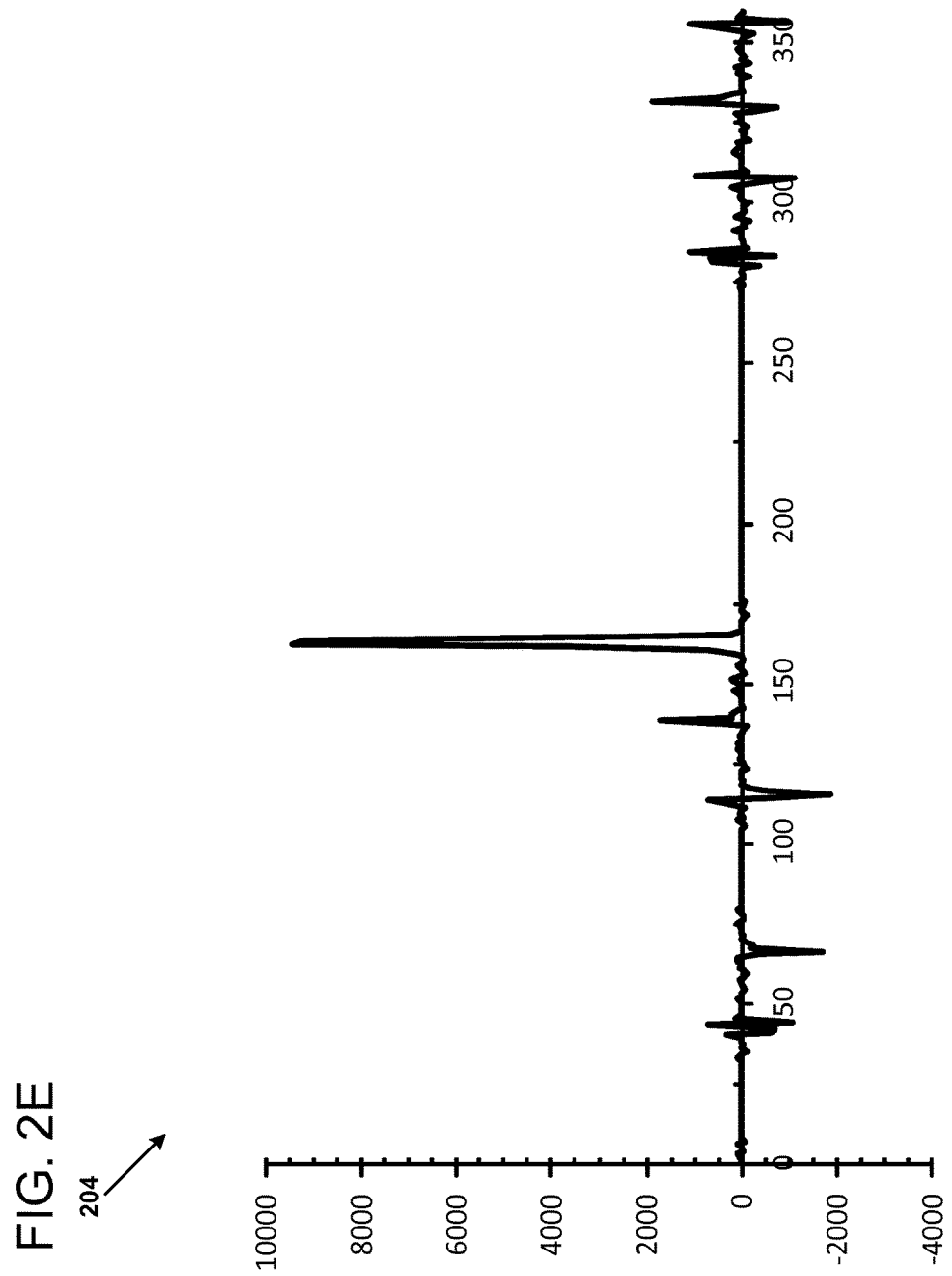
Figure 2F:
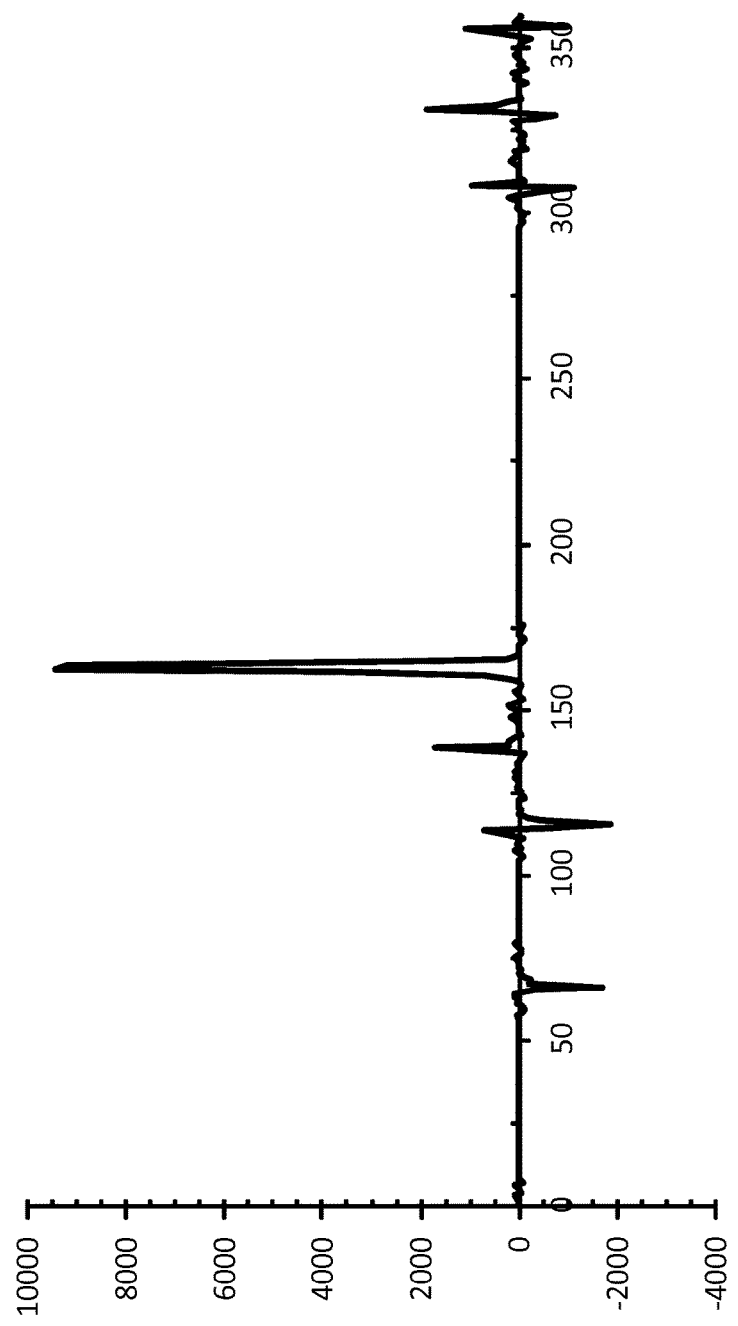
Figure 2G:
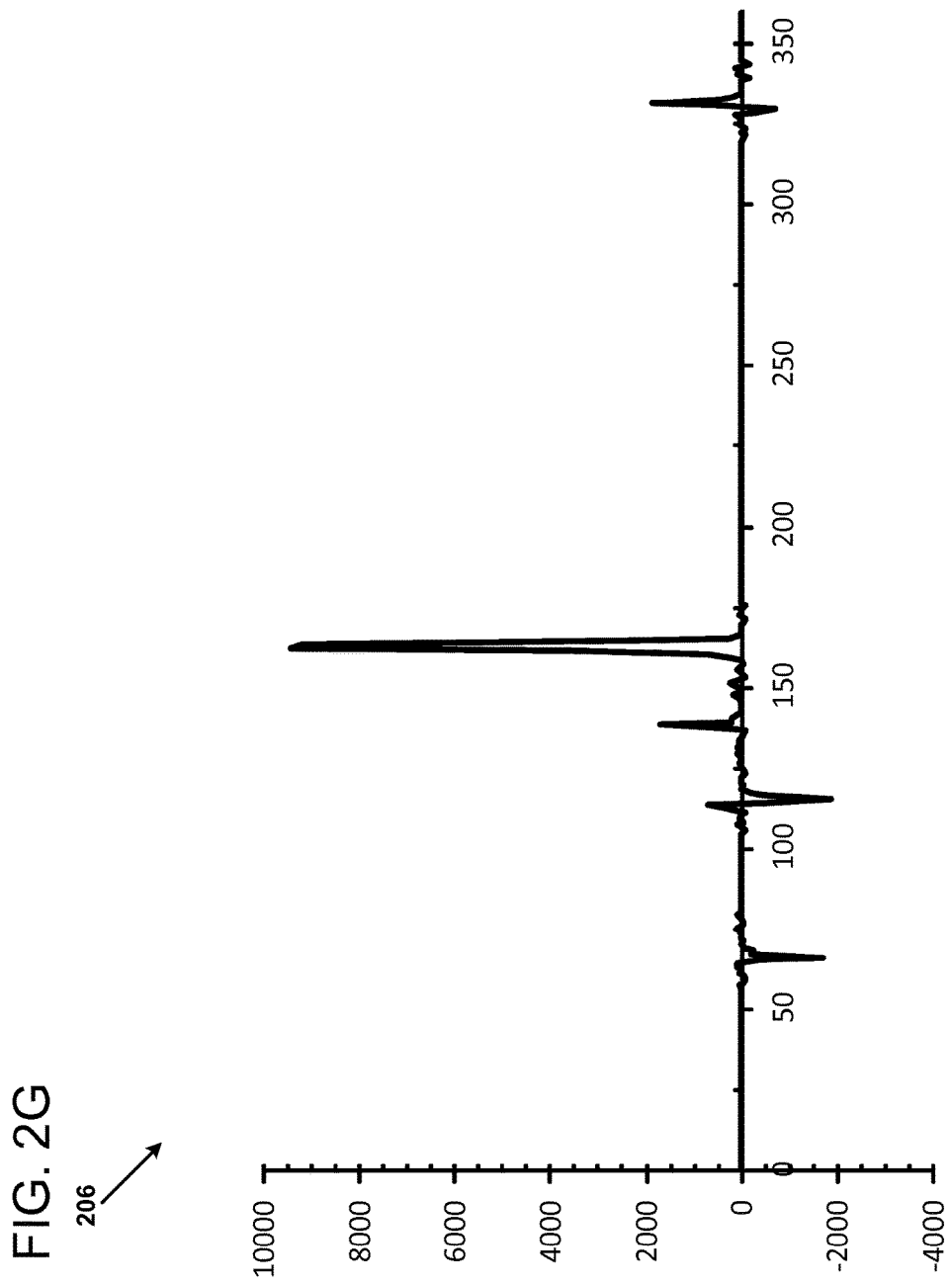
Figure 2H:
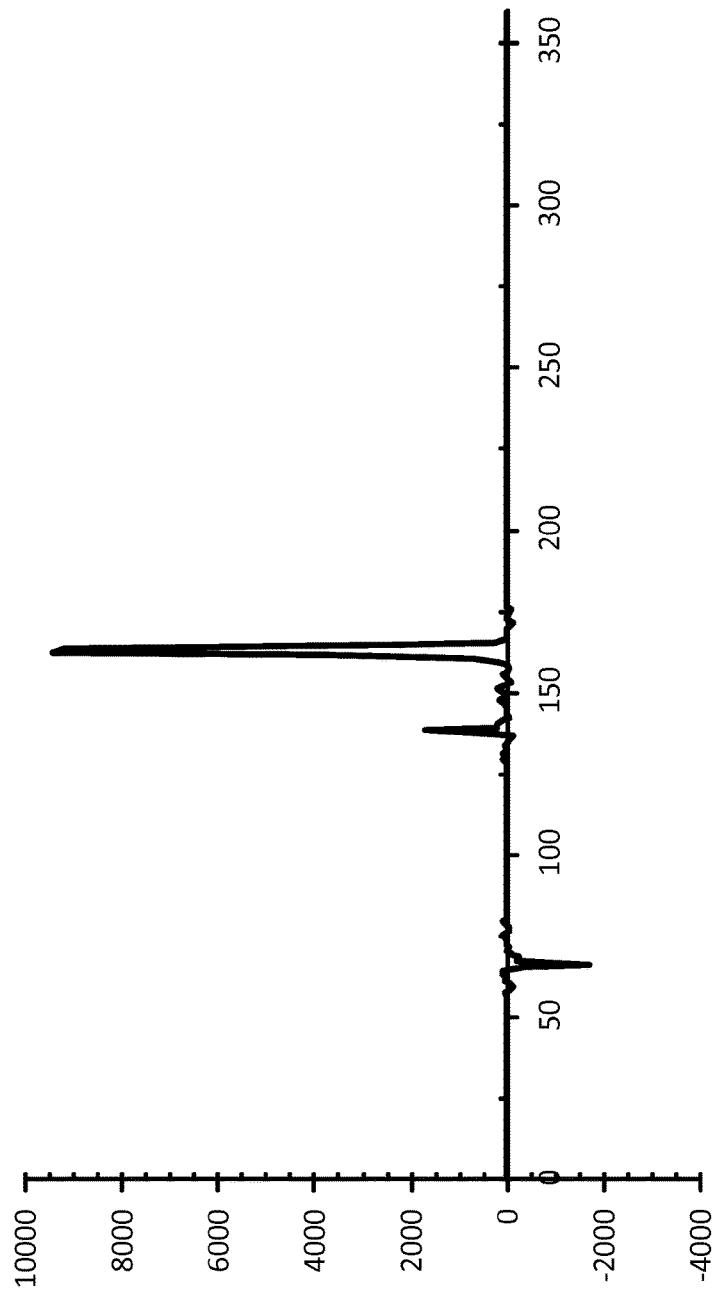

Examples of iteratively removing symmetric pairs (e.g., symmetric pairs 240 or 241) from the transformed intensity data 225 are illustrated in FIGS. 2C-2I. For example, transformed intensity data after removing the first pair 240 is illustrated in FIG. 2C, while transformed intensity data after removing the second pair 241 are shown in FIG. 2D. FIGS. 2E-2H illustrate subsequent removal of symmetric pairs from the transformed intensity data.

Figure 2I:
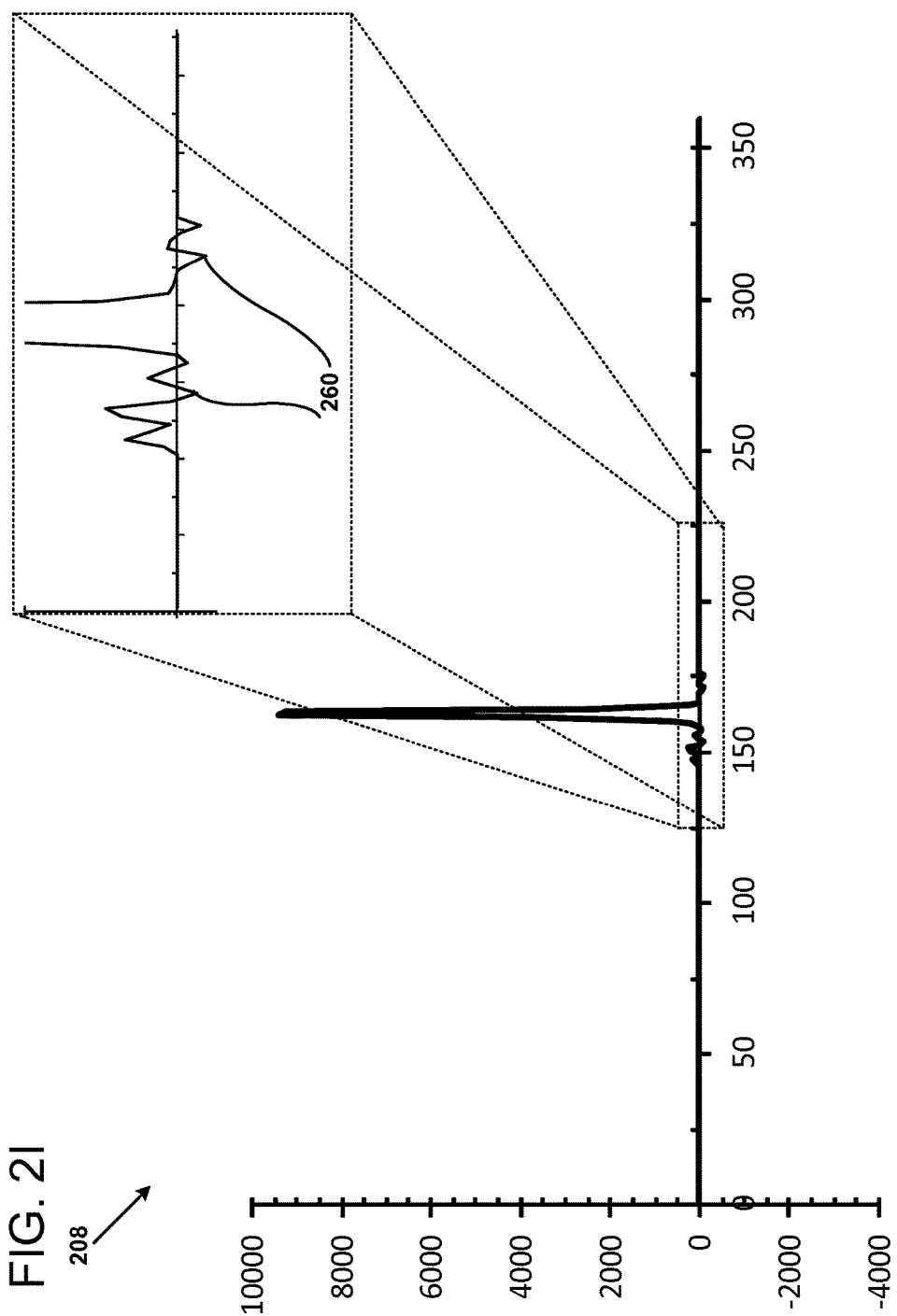

The chart 208 of FIG. 2I illustrates filtered transformed intensity data after all the identified symmetric pairs have been removed. As shown, a few small negative data artifacts 260 remain in the filtered transformed intensity data.

In some examples the filtered transformed intensity data are further filtered to remove negative intensities (e.g., the negative data artifacts 260) in the transformed data. An example of the filtered transformed intensity data after such further filtering, thereby producing reduced-noise data, is illustrated by FIG. 2J. As shown in the chart 209 of FIG. 2J, the reduced noise data exhibits "real" data 270, with a substantial portion of data artifacts and noise removed.

V. Exemplary Method of Validating Peaks in Transformed Data Using a PRS

FIG. 3 is a flow chart 300 that outlines an exemplary method of validating peaks by analyzing untransformed data that is used to generate transformed intensity data, as can be used in some examples of the disclosed technology.

At process block 310, one or more peaks that remain in transformed intensity data are identified. For example, peaks can be identified for validation based on the magnitude of the data in each of the time segment bins. Each of the identified peaks will be validated in comparison to the pseudorandom sequence to determine which peaks should be validated and thus not removed. In some examples, symmetric pairs have already been removed from the transformed intensity data (e.g., using techniques similar to those discussed above regarding the method outlined in FIG. 1). In other examples, symmetric pairs are not removed from the transformed intensity data prior to identifying peaks. After identifying one or more peaks, the method proceeds to process block 320.

At process block 320, one of the peaks identified at process block 310 is selected to be validated. Once a peak has been selected in the transformed data, the method proceeds to process block 330.

At process block 330, a bit of the pseudorandom sequence is selected to compare to peaks in the untransformed data, starting with the first bit identified at process block 320 and then proceeding to subsequent bits of the PRS on subsequent executions of process block 330. The peaks can be identified starting with time segment bins centered about the apex of the peak selected at process block 320. If the corresponding bit of the PRS is a 0, then there may or may not be a corresponding peak in the untransformed data. Thus, the method can proceed back to process block 330 to get the next bit of the PRS. Alternatively, if the corresponding next bit of the PRS is a 1, then there should be a corresponding peak in the untransformed data in order for the selected peak to be considered valid.

The untransformed data is analyzed. If there is no peak in a time segment bin corresponding to a 1 bit of the PRS, then the selected peak is designated as invalid (and thus can be removed), and the method proceeds to process block 340 in order to designate the selected peak as being invalid and/or to remove the selected peak from the filtered data. Similar techniques to those discussed above regarding process block 140 can be employed to remove or filter the data, thereby producing modified data. In some examples, negative intensity values, or values less than a certain threshold, are also removed, to produce reduced-noise data.

Alternatively, if there is a peak corresponding to a 1-bit time segment bin for each bit of the pseudorandom sequence, then the selected peak is designated as valid (and thus should be retained) at process block 350.

After determining that the selected peak is valid or invalid, additional peaks of those peaks identified at process block 310 are validated by repeating the acts of process blocks 320, 330, and 340 or 350 for each of the additional peaks. In some examples, the time segment bins used to compare the pseudorandom sequence can be shifted relative to the apex of each selected peak.

An evaluation (e.g., by identifying and/or characterizing molecules) of a sample used to produce the transformed intensity data can be performed using the validated peaks.

VI. Experimental Results for Validating Peaks in Filtered Transformed Data

FIGS. 4A through 4G are charts 400-406 depicting an experimental data set as data is transformed and peaks in the data are validated. The charts 400-406 illustrate an example of correlating the encoding pseudorandom sequence (PRS) "100110101111000" (reference number 410) when there are multiple "real" data signals present in the untransformed (or "raw") intensity data 420 (e.g., before applying a Hadamard transform to the data), as can be performed in certain embodiments of the disclosed technology. As shown in the chart 400 of FIG. 4A, there are a number of peaks (e.g., peaks 421, 422, and 423) in the untransformed intensity data 420.

FIG. 4B is a chart 401 that illustrates transformed intensity data 430 after applying a Hadamard transform to the untransformed intensity data 420. As shown, a number of peaks, including peak 431, are included in the transformed data 430.

FIG. 4C is a chart 402 illustrating filtered transformed data 440 after removing symmetric pairs from the transformed data 430 according to the PRS 410. As shown, a number of peaks 441-443 are present in the filtered transformed data 440. The techniques discussed above regarding process blocks 120-150 of the method of FIG. 1 can be employed to filter symmetric pairs from the transformed intensity data, or other suitable filtering methods can be employed.

FIG. 4D is a chart 403 that indicates a corresponding peak 421 in the untransformed intensity data 420 that will be compared to the selected peak 441 in the filtered transformed data 440 for validation. Dashed lines indicate that the untransformed data has been aligned with time segment bins corresponding to the peak 421 and the PRS 410. As shown in FIG. 4D, a first time segment bin is associated with the corresponding peak 421 and the first bit the PRS 410, which is indicated by a circle. This can be performed by determining the x value (drift time scan) of the apex of the peak to be validated (e.g., at $x_1$=123, as shown in FIG. 4D). Then, by moving to the right along the x-axis by one segment length (24 drift time scans, as shown in FIG. 4D, another apex of a peak at is searched for at that x value (e.g., at $x_2$=$x_1$+24, or 147). The apexes of peaks at different time segment bins may not match exactly, but a threshold can be used to determine how close an apex in the data should be to the x value modulo segment length.

It should be noted that the untransformed data 420 is cyclic. Thus, the time segment bins (indicated by the dashed lines) may not necessarily start at the first time point (e.g., time 0) and end at the end time point (e.g., time 360). The data can "wrap around," thus allowing a segment of time to exist at both the end and beginning of the x-axis.

As shown in FIG. 4D, each 1 bit of the PRS corresponds to a peak in the untransformed data 420. While there are also some peaks in time segment bins corresponding to 0 bits of the PRS, this is acceptable, as those time segment bins can have peaks according to the method outlined in FIG. 3. Thus, peak 441 of FIG. 4C is validated as a real peak in the transformed intensity data.

FIG. 4E is a chart 404 illustrating a comparison of using the PRS 410 for a second selected peak 442, which corresponds to a peak 422 in the untransformed data. As shown, the first bit of the PRS 410 (circled) is aligned with the corresponding position of the peak 442 in the untransformed data. (That is, the PRS 410 has been shifted to the right one time segment bin relative to the comparison shown in FIG. 4D). The iterative comparison described above regarding process block 330 is carried out for the second peak 442. As with the first peak 441, there is a peak corresponding to each 1-bit time segment bin according to the PRS 410, and thus, peak 442 is also validated as a real peak in the transformed intensity data using the PRS 410.

FIG. 4F is a chart 405 illustrating a comparison using the PRS for a third selected peak 443, which corresponds to peak 423 in the untransformed data 420. As shown, the first bit of the PRS (circled) is aligned with the corresponding position of the peak 423 in the untransformed data 420. (That is, the PRS has been shifted to the right five time segment bins relative to the comparison shown in FIG. 4D). The iterative comparison described above regarding process block 330 is carried out for the third peak 443. In contrast to the first two peaks 441 and 442, there are a number of peaks missing in the untransformed data, which are each indicated by an "x" in the chart 405 of FIG. 4F. Thus, the third selected peak 443 is determined to not be a valid peak, and will be designated as invalided (e.g., using techniques discussed above regarding process block 340).

Figure 4G:
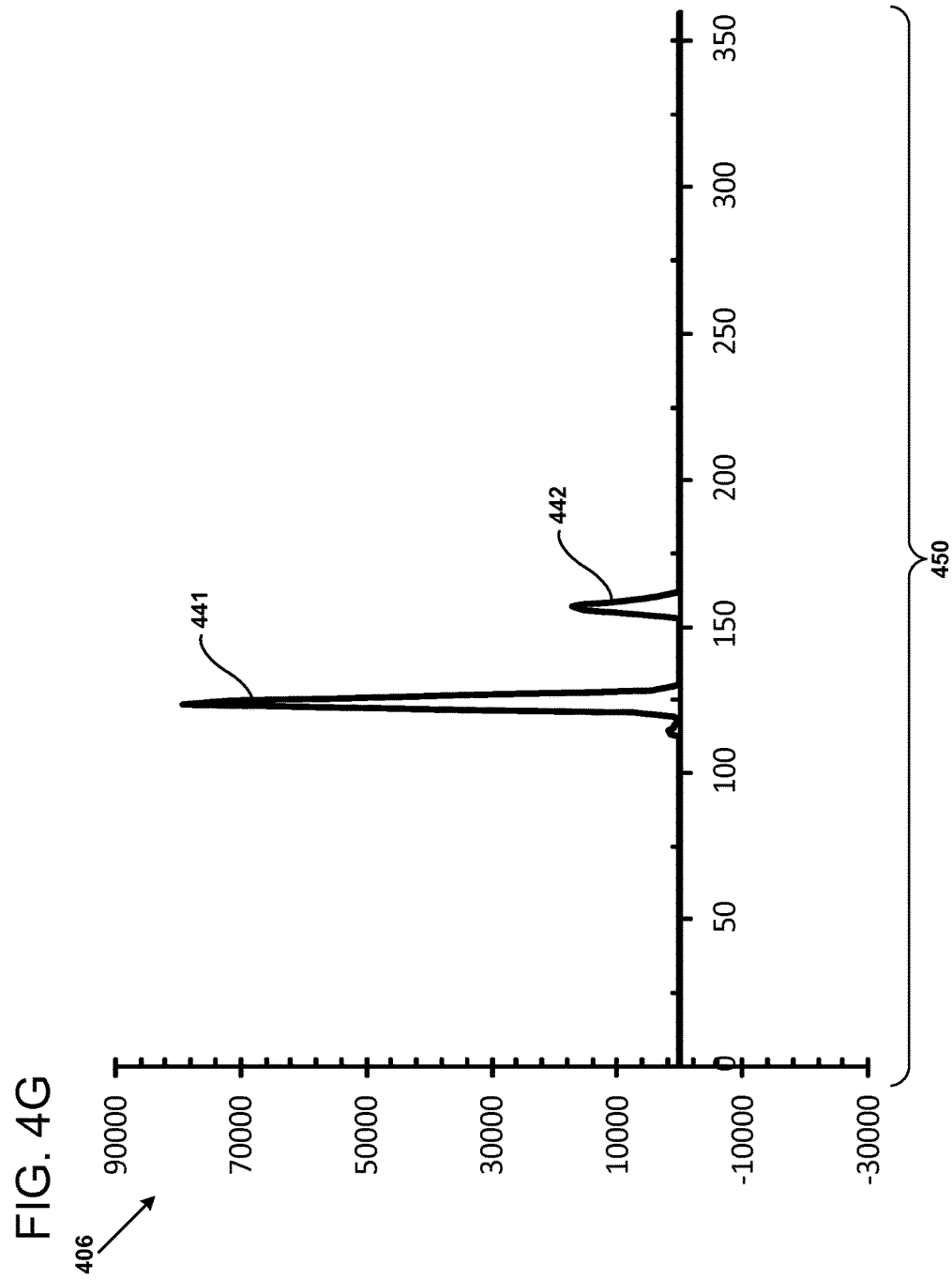

An example of modified data 450 produced according to the method of FIG. 3 is illustrated in the chart 406 of FIG. 4G. As shown, only two peaks 441 and 442 from the filtered transformed data 440 are still present in the modified data 450.

VII. Exemplary Method of Filtering Detector Data Generated by PRS Modulation

FIG. 5 is a flow chart 500 that illustrates an exemplary method of identifying peaks in data generated by modulation using a pseudorandom sequence, and transforming the data by an invertible transform (e.g., a Hadamard transform), as can be used in certain embodiments of the disclosed technology.

At process block 510, intensity data generated by a detector responsive to a signal modulated using a pseudorandom sequence is received. The intensity data can be received in a computing environment using an I/O port, a network, or other suitable hardware. In some examples, the intensity data are based on a received signal generated by a detector coupled to a mass spectrometer. The mass spectrometer can allow for introduction of analytes into the spectrometer according to a pseudorandom sequence. A description of the pseudorandom sequence used to modulate the signal can also be received at process block 510.

After receiving the intensity data and the pseudorandom sequence used to generate the intensity data, the method proceeds to process block 520.

At process block 520, a Walsh-Hadamard transform (also called a Hadamard transform) is applied to the intensity data received at process block 510. An exemplary equation for applying a Hadamard transform for the data is shown below:

$$\hat{I}_{trans}{}^T = H_n \hat{I}$$

where $\hat{I}$ is a vector of the intensity data received at process block 510, $H_n$ is a Hadamard matrix of size n×n (selected according to the length of the pseudorandom sequence used to encode the intensity data), and $\hat{I}_{trans}$ is the transformed data according the Hadamard matrix. As will be readily apparent to one of ordinary skill in the art, the application of a Hadamard transform will vary depending on the number of bits in the pseudorandom sequence used to encode the intensity data. Applying the Hadamard transform introduces a number of artifacts into the resulting transformed data. These artifacts reduce the signal-to-noise ratio of resulting data, and can be removed as discussed below regarding process blocks 530, 540, and 550.

In some examples, an input/output (I/O) or network interface in a computing environment can be used to receive intensity data and apply an invertible transform to the intensity data. The transformed intensity data can be generated by, for example, applying a Hadamard transform to intensity data received from a detector coupled to an ion mass spectrometer.

After generating the transformed intensity data, the method proceeds to process block 530.

At process block 530, one or more a symmetric pairs in the transformed data from process block 520 are identified. In some examples, knowledge of the pseudorandom sequence that was applied when generating and receiving the analytes at process block 510 can be used to identify symmetric pairs in the transformed data. In some examples, a symmetric pair in the transformed data can be identified based on symmetry of the pairs. For example, peaks of a transformed intensity data that are substantially identical across the x-axis (i.e., y=0) can be identified as symmetric pairs. In some examples, the transformed data are analyzed to identify symmetric peaks corresponding to zeros and ones in the transformed data.

Once one or more symmetric pairs have been identified in the transformed data, the method proceeds to process block 540.

At process block 540, data associated with a symmetric pair that were identified at process block 530 are filtered or removed to produce modified data. In some examples, data for a corresponding time segment for each of the peaks of the symmetric pair are set to zero. In some examples, data for the symmetric peaks are subtracted from the corresponding portion of the time period.

At process block 550, the filtered transformed intensity data are further filtered to remove negative intensities in the transformed data. After filtering the negative data artifacts, the method proceeds to process block 560.

At process block 560, peaks in the data are validated in comparison to a pseudorandom sequence (e.g., pseudorandom sequence 230) used to encode the intensity data. In some examples, peaks in the reduced noise data are compared for each time segment corresponding to the pseudorandom sequence. For any time segment "1" value in the pseudorandom sequence, there should be a corresponding peak in the untransformed raw data. If a corresponding peak is not found in the raw data, then the peak in question is marked as invalidated and is removed from the reduced noise data. For time segments corresponding to a "0" value in the pseudorandom sequence, there may or may not be a peak, meaning that the "0" value time segments can be ignored. A further detailed example of validating peaks in filtered transformed data is explained below regarding the exemplary method of FIG. 3, although other suitable techniques can also be used. After a number of validated peaks are produced at process block 560, the method proceeds to process block 570.

At process block 570, data corresponding to peaks that were not validated at process block 560 are removed from the reduced noise data. Similar techniques used to those described above for removing peaks of symmetric pairs regarding process block 540 can be used to remove non-validated peaks.

The data from process block 570 represents the intensity values for an associated m/z (mass to charge ratio) value. These data can be used to evaluate the sample that was used to produce the analytes detected by the spectrometer. As will be readily understood by those of ordinary skill in the art, along with the filtered transformed data and/or reduced noise data, additional information may be used to identify, quantify, and characterize the sample. As the filtering performed at process blocks 530-570 removes artifacts, noise, and invalid data from the transformed data, the data generated thereby can be used to more accurately evaluate (e.g., identify, characterize, and/or quantify) the sample. Methods used to evaluate the sample using the validated data will be readily apparent to one of ordinary skill in the relevant art.

VIII. Exemplary Mass Spectrometry Apparatus

Figure 6:
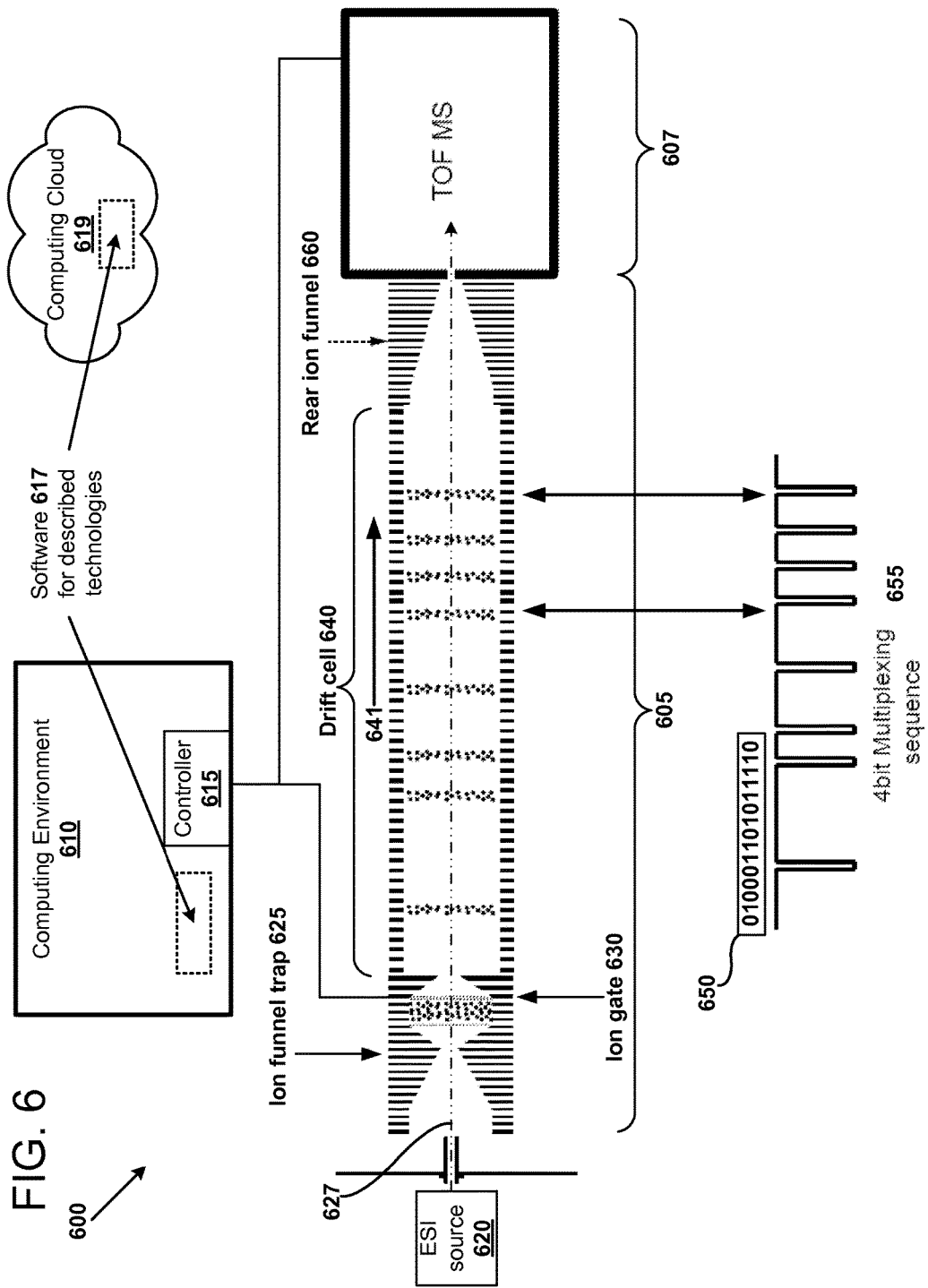
FIG. 6 illustrates a spectrometry system as can be used in certain embodiments of the disclosed technology.

FIG. 6 illustrates a system 600 comprising an ion mobility spectrometer 605 and a time-of-flight mass spectrometer 607 coupled to a computing environment 610 with a controller 615, as can be used in certain examples of the disclosed technology. The computing environment 610 includes one or more processors, memory, and computer-readable storage media that can store software 617 for implementing the disclosed technologies. In some examples, at least a portion of the software 617 can be stored and/or executed in a server or a computing cloud 619 at a location remote from the spectrometer 605. In some examples, field programmable gate arrays (FPGAs) or other reconfigurable logic devices can be used to augment, or instead of, the processors and/or memory. The computing environment can include some or all aspects of the computing environment 700 as described below regarding FIG. 7. An Agilent model 6224 time-of-flight mass spectrometer or Agilent model 6538 quadrupole time-of-flight mass spectrometer can be used as the time-of-flight mass spectrometer 607, although any other suitable spectrometers can also be used.

As shown in FIG. 6, an electrospray ionization (ESI) source 620 having a heated capillary provides ionized analytes produced from a sample under analysis. The ESI source 620 is operatively coupled to allow particles to travel into an ion funnel trap 625 before entering the ion mobility spectrometer 605. The analytes travel through the ion funnel trap 625 before reaching a region gated with an ion gate 630. In some examples, the ion gate(s) 630 are a Bradbury-Nielsen shutter, while in other examples, other suitable gating technology, such as dual grids or varying designs, can be used. The generated analytes generally travel through the spectrometers 605 and 607 along the path indicated dashed line 627.

Opening and closing of the ion gate(s) 630 is modulated by the controller 615 responsive to the computing environment 610. Thus, the ion gate(s) 630 can control introduction of analyte ions into a drift cell 640 in accordance with a pseudorandom sequence "010001101011110" (reference number 650). This pseudorandom sequence 650 can be referred to as a 4-bit multiplexing sequence, as there are $2^4-1$ ($2^n-1$, where n=4) bits in the sequence. The pseudorandom sequence 650 is applied in reverse order to the modulate operation of the ion gate(s) 630 sequentially over time. For example, the reversed seven rightmost bits of the pseudorandom sequence 650 ("0111101") correspond to sequentially sending the commands close, open, open, open, open, close, and open to the ion gate 630. In some examples, the gate open command opens the ion gate(s) for a portion of the time period allocated to the corresponding bit of the pseudorandom sequence. Thus, the ion gate(s) 630 are open during at least a portion of a corresponding "1" period, thereby allowing analytes to travel into the drift cell 640. Conversely, a zero value corresponds to the ion gate(s) 630 being closed for the entirety of a corresponding time period, thereby not allowing analytes to enter the drift cell 640 during the corresponding time segment. The drift cell 640 is operable to apply an electric field in the direction indicated by an arrow 641.

Analytes (e.g., ions produced by the ESI transmitter) further travel through the length of the drift cell 640 and are introduced into a rear ion funnel 660. The ion funnel 660 is operatively coupled to one or more electrical and/or magnetic multi-pole elements (e.g., quadrupole elements, DC quadrupole elements, octopole elements, or other suitable multi-pole elements), which allows selected analytes within a certain range of mass-to-charge ratios (m/z) to reach the time-of-flight mass spectrometer 607. The time-of-flight mass spectrometer uses well-known elements, such as ion extractors, reflectrons, and a detector, to produce intensity values. As will be readily understood to those of ordinary skill in the relevant art, any suitable detector can be employed to detect analytes, for example, a microchannel plate detector. In some examples, additional components of the ion mobility mass spectrometer 605 and a time-of-flight mass spectrometer 607 can include inputs and outputs for gases, such as sample gas outlet(s) and a drift gas inlet(s).

Also illustrated in FIG. 6 is application of a 4-bit multiplexing sequence 655 according to the pseudorandom sequence 650. Packets of analytes are shown traveling through the drift cell 640 that have been released by the ion gate(s) 630 according to the pseudorandom sequence 650. Time segments of the total multiplexing time sequence are allotted to each bit of the pseudorandom sequence. Each of the time segments (also called "bins") can be further subdivided into time periods (or "sub-bins") (e.g., sub-divided in 10 sub-bins). The first "1" of the PRS is applied to the ion gate(s) 630 by pulsing the ion gate for the first one tenth of the time segment (a first sub-bin), followed by the ion gate(s) 630 being closed for the remainder of the time segment (nine subsequent sub-bins). For time segments of the pseudorandom sequence corresponding to zero, the ion gate(s) 630 remain closed for the entire time segment (e.g., for ten sub-bins).

In some examples of the disclosed technology, two aspects are used in an analysis of analyte intensity values. The first aspect is the encoding pseudorandom sequence (PRS) bit string, which in some examples can be constructed based using maximal length shift registers. In some examples, the PRS is a series of "1s" and "0s" that is of length $2^{n-1}$, and has the property that there is one less "0" than "1." The second aspect is the length of an encoding segment. The length of a segment represents a temporal extension of the PRS in an attempt to separate the events of releasing and collecting ions. For example, if the length of a segment is ten, then when a "0" is found in the PRS, the sequence applied to the ion gate is filled with ten zeroes, or 0000000000. When there is a "1" in the PRS, the sequence applied to the ion gate is filled with nine 0's and one 1, or 0000000001. In some examples, a sequence other than a PRS may be used.

IX. Exemplary Computing Environment

Figure 7:
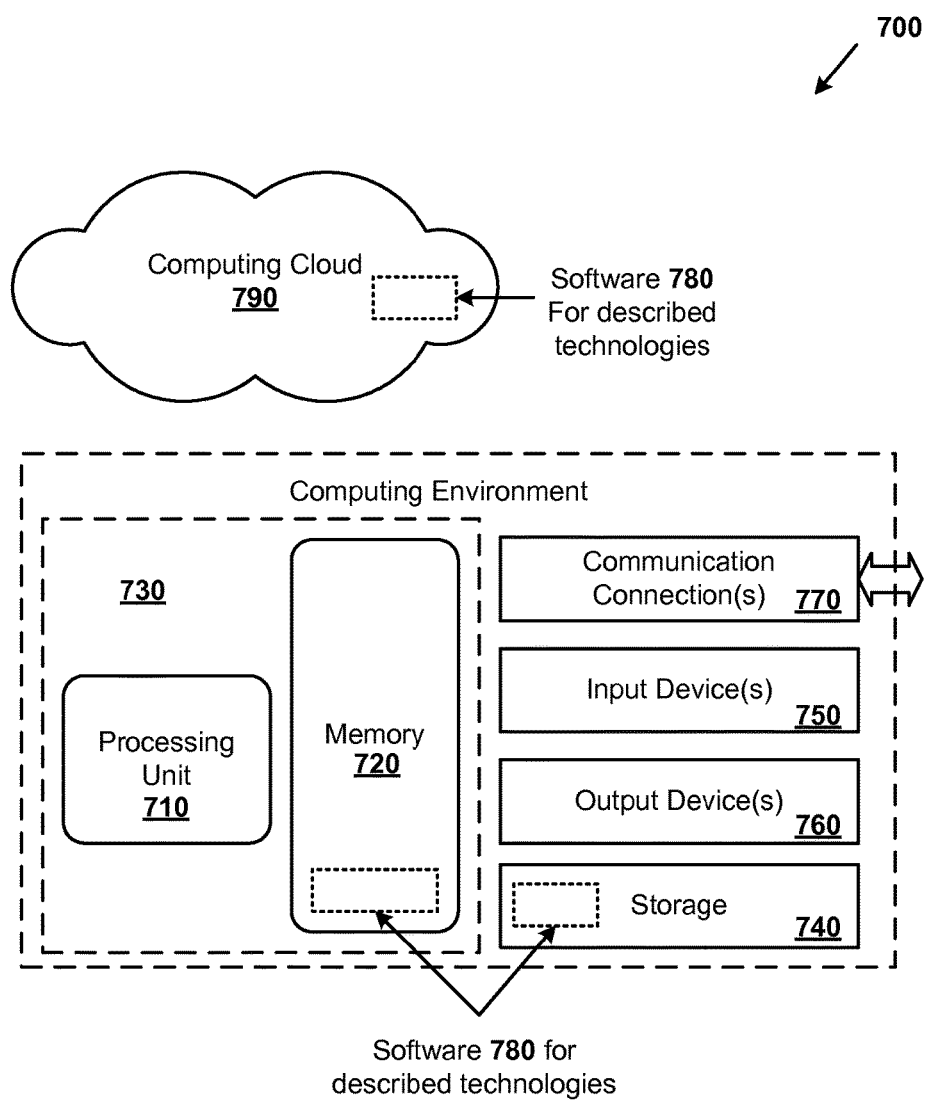
FIG. 7 illustrates a generalized example of a suitable computing environment in which described embodiments, techniques, and technologies can be implemented.

FIG. 7 illustrates a generalized example of a suitable computing environment 700 in which described embodiments, techniques, and technologies can be implemented. For example, the computing environment 700 can be used to receive intensity data, apply invertible matrix transforms, and filter transformed data, as described above.

The computing environment 700 is not intended to suggest any limitation as to scope of use or functionality of the technology, as the technology can be implemented in diverse general-purpose or special-purpose computing environments. For example, the disclosed technology can be implemented with other computer system configurations, including hand held devices, multiprocessor systems, microprocessor-based or programmable consumer electronics, network PCs, minicomputers, mainframe computers, and the like. The disclosed technology can also be practiced in distributed computing environments where tasks are performed by remote processing devices that are linked through a communications network. In a distributed computing environment, program modules can be located in both local and remote memory storage devices.

With reference to FIG. 7, the computing environment 700 includes at least one central processing unit 710 and memory 720. In FIG. 7, this most basic configuration 730 is included within a dashed line. The central processing unit 710 executes computer-executable instructions and can be a real or a virtual processor. In a multi-processing system, multiple processing units execute computer-executable instructions to increase processing power and as such, multiple processors can be running simultaneously. In some examples, FPGAs or other reconfigurable logic devices can be used to augment, or instead of, the central processing unit 710 and/or memory 720. The memory 720 can be volatile memory (e.g., registers, cache, RAM), non-volatile memory (e.g., ROM, EEPROM, flash memory, etc.), or some combination of the two. The memory 720 stores software 780 that can, for example, implement the technologies described herein. A computing environment can have additional features. For example, the computing environment 700 includes storage 740, one or more input devices 750, one or more output devices 760, and one or more communication connections 770. An interconnection mechanism (not shown) such as a bus, a controller, or a network, interconnects the components of the computing environment 700. Typically, operating system software (not shown) provides an operating environment for other software executing in the computing environment 700, and coordinates activities of the components of the computing environment 700.

The storage 740 can be removable or non-removable, and includes magnetic disks, magnetic tapes or cassettes, CD-ROMs, CD-RWs, DVDs, or any other medium which can be used to store information and that can be accessed within the computing environment 700. The storage 740 stores instructions for the software 780 and data (e.g., measurement data or correlation data), which can be used to implement technologies described herein.

The input device(s) 750 can be a touch input device, such as a keyboard, keypad, mouse, touch screen display, pen, or trackball, a voice input device, a scanning device, or another device, that provides input to the computing environment 700. For audio, the input device(s) 750 can be a sound card or similar device that accepts audio input in analog or digital form, or a CD-ROM reader that provides audio samples to the computing environment 700. The output device(s) 760 can be a display, printer, speaker, CD-writer, or another device that provides output from the computing environment 700.

The communication connection(s) 770 enable communication over a communication medium (e.g., a connecting network) to another computing entity. The communication medium conveys information such as computer-executable instructions, compressed graphics information, video, or other data in a modulated data signal.

The input device(s) 750, output device(s) 760, and communication connection(s) 770 can be used with a control system to control inputs and/or outputs for a spectrometer. For example, input devices can be used with a control system for modulating an ESI transmitter, an ion gate, or gas inputs and outputs of a mass spectrometer. Further, output devices can be used with a control system for sampling or removing analytes or gases from a spectrometry system. In some examples, a communication connection 770, such as an RS-232, USB, Ethernet, or other suitable connection, is used to control spectrometer operation and detection.

Some embodiments of the disclosed methods can be performed using computer-executable instructions implementing all or a portion of the disclosed technology in a computing cloud 790. For example, applying Hadamard transforms and filtering data by removing symmetric pairs can be performed on servers located in the computing cloud 790.

Computer-readable media are any available media that can be accessed within a computing environment 700 and include, by way of example, and not limitation, include memory 720 and/or storage 740. As should be readily understood, the term computer-readable storage media includes the media for data storage such as memory 720 and storage 740, and not transmission media carrying modulated data signals or transitory signals.

Any of the methods described herein can be performed via one or more computer-readable media (e.g., storage or other tangible media) comprising (e.g., having or storing) computer-executable instructions for performing (e.g., causing a computing device to perform) such methods. Operation can be fully automatic, semi-automatic, or involve manual intervention.

Having described and illustrated the principles of our innovations in the detailed description and accompanying drawings, it will be recognized that the various embodiments can be modified in arrangement and detail without departing from such principles. It should be understood that the programs, processes, or methods described herein are not related or limited to any particular type of computing environment, unless indicated otherwise. Various types of general purpose or specialized computing environments can be used with or perform operations in accordance with the teachings described herein. Elements of embodiments shown in software can be implemented in hardware and vice versa.

In view of the many possible embodiments to which the principles of the disclosed invention may be applied, it should be recognized that the illustrated embodiments and their equivalents are only preferred examples of the invention and should not be taken as limiting the scope of the invention.

We claim:

1. A method comprising:
by a computer:
receiving intensity data generated by a detector in response to receiving a signal modulated by a pseudorandom sequence (PRS) over time;
applying a Hadamard transform selected based on the length of the PRS to the intensity data to produce Hadamard transformed data;
identifying at least one pair of symmetric intensity peaks in the Hadamard transformed data using the PRS that was used to generate the Hadamard transformed data; and
filtering the identified pair of symmetric peaks from the transformed data, thereby producing filtered data.

2. The method of claim 1, further comprising removing negative data from the filtered data.

3. The method of claim 1, further comprising validating one or more peaks in the filtered data using the PRS.

4. The method of claim 3, further comprising filtering one or more peaks in the filtered data that were designated as not valid using the PRS.

5. The method of claim 3, wherein the validating further comprises:
if a bit of the PRS corresponding to a respective time segment bin is a 1, then confirming existence of a peak in untransformed data associated with its respective time segment bin.

6. The method of claim 3, wherein the validating further comprises:
if a bit of the PRS corresponding to a respective time segment bin is a 0, then ignoring whether there is a peak in untransformed data associated with its respective time segment bin.

7. An apparatus for performing the method of claim 1, the apparatus comprising:
a spectrometer instrument system comprising a gate configured to modulate introduction of analytes to a detector according to the PRS; and
logic coupled to the detector, the logic operable to cause the gate to modulate introduction of the analytes to the detector.

8. The apparatus of claim 7, wherein:
the logic comprises one or more processors, one or more field-programmable gate arrays (FPGAs), or one or more processors and one or more FPGAs; and
the logic is operable to cause the processors, the FPGAs, or the processors and the FPGAs to perform the identifying and the filtering.

9. The method of claim 1, further comprising:
analyzing the filtered data to characterize a sample used to produce the Hadamard transformed data.

10. The method of claim 1, further comprising:
applying the pseudorandom sequence (PRS) to a sample to generate the transformed intensity data.

11. A method comprising:
by a computer:
receiving intensity data generated by a detector in response to receiving a signal modulated by a pseudorandom sequence (PRS) over time;
applying a Hadamard transform selected based on the length of the PRS to the intensity data to produce Hadamard transformed data;
identifying peaks in the Hadamard transformed data;
validating the identified peaks in the Hadamard transformed data using the PRS, producing valid peaks and invalid peaks; and
filtering the invalid peaks using the PRS.

12. The method of claim 11, wherein the transformed data is generated by applying a Hadamard transform to untransformed data, and wherein the validating further comprises:
identifying one or more peaks in the transformed data,
selecting at least one of the identified peaks to validate using the PRS;
if there is a peak in the untransformed intensity data at a first portion of the untransformed data corresponding to a 1 bit of the PRS, designating the selected peak as valid; and
if there is not a peak in the untransformed data at the first portion corresponding to a 1 bit of the PRS, designating the selected peak as invalid.

13. The method of claim 12, wherein the validating further comprises:
selecting a second at least one of the identified peaks to validate using the PRS;
if there is a peak in the untransformed data at a second portion of the unfiltered data corresponding to a 1 bit of the PRS, designating the selected peak as valid; and
if there is not a peak in the untransformed data at the second portion corresponding to a 1 bit of the PRS, designating the second peak as invalid.

14. The method of claim 12, further comprising defining a plurality of time portions in the untransformed data according to the PRS.

15. The method of claim 12, wherein the portions are defined relative to the first selected peak.

16. The method of claim 11, further comprising repeating the validating and the filtering the invalid peaks according to respective portions of the PRS.

17. The method of claim 11, wherein the identified peak is designated as valid even if there are peaks in untransformed data at any portion corresponding to a 0 bit of the PRS.

18. The method of claim 11, further comprising, if the PRS has a 0 at a corresponding portion of untransformed data, then ignoring whether there is a peak in the untransformed data.

19. An apparatus for performing the method of claim 11, the apparatus comprising:
a spectrometer instrument system comprising a gate configured to modulate introduction of analytes to a detector according to the PRS; and logic coupled to the detector, the logic operable to cause the gate to modulate introduction of the analytes to a detector configured to receive the analytes.

20. The apparatus of claim 19, wherein:
the logic comprises one or more processors, one or more field-programmable gate arrays (FPGAs), or one or more processors and one or more FPGAs; and
the logic is operable to cause the processors, the FPGAs, or the processors and the FPGAs to perform the identifying and the filtering.

21. A method comprising:
by a computer:
applying a Hadamard transform selected based on the length of a pseudorandom sequence (PRS) to intensity data to produce Hadamard transformed data, the intensity data having been generated by a detector in response to receiving a signal modulated by the PRS over time;
identifying at least one pair of symmetric peaks in Hadamard transformed data using a pseudorandom sequence (PRS) that was used for producing the Hadamard transformed data;
filtering the identified pair of symmetric peaks from the transformed data;
removing negative data from the filtered data;
validating peaks in the filtered data using the PRS; and
filtering the peaks that were not validated with the PRS.

22. The method of claim 21, wherein the validating comprising identifying peaks in untransformed data used to generate the Hadamard transformed data.

23. The method of claim 21, wherein the validating further comprises:
if a bit of the PRS corresponding to a respective time segment bin is a 1, then confirming existence of a peak in untransformed data associated with its respective time segment bin.

24. The method of claim 21, wherein the validating further comprises:
if a bit of the PRS corresponding to a respective time segment bin is a 0, then ignoring whether there is a peak in untransformed data associated with its respective time segment bin.

25. The method of claim 21, further comprising:
receiving untransformed data generated by a detector in response to receiving a signal modulated by the pseudorandom sequence (PRS) over time; and
applying a Hadamard transform to the intensity data to produce the Hadamard transformed data.

26. The method of claim 21, wherein the identifying the at least one symmetric pair comprises:
comparing similarities of two intensity peaks in the transformed data; and
based on the comparing, identifying the two intensity peaks as the at least one pair of symmetric intensity peaks.

27. The method of claim 21, wherein the identifying the at least one symmetric pair comprises:
comparing similarities of two intensity peaks in the transformed data to determine that the two intensity peaks are substantially symmetrical; and
based on the comparing, identifying the two intensity peaks as the at least one pair of symmetric intensity peaks.

28. The method of claim 21, wherein the identifying the symmetric pair comprises:
identifying a first peak of the at least one pair being located in a first portion of the Hadamard transformed data, the first portion corresponding to a first value of the PRS;
identifying a second peak of the at least one pair as being located in a portion of the Hadamard transformed data, the second portion corresponding to a second value of the PRS; and
based on the identifying the first and second peaks, identifying the first peak and the second peak as the at least one pair of symmetric intensity peaks.

29. The method of claim 21, wherein the identifying the at least one symmetric pair comprises identifying a plurality of pairs of symmetric intensity peaks, wherein each of the plurality of pairs corresponds to a different pair of a complementary time segment bins associated with the PRS.

30. The method of claim 21, wherein the identifying the at least one symmetric pair comprises analyzing the Hadamard transformed data according to a number of time segment bins associated with the PRS.

31. The method of claim 21, wherein the filtering the not validated peaks produces validated data, the method further comprising:
sending untransformed data to a remote server or computing cloud; and
receiving the filtered data or the validated data from the remote server or the computing cloud.

32. The method of claim 21, wherein the filtering the not validated peaks produces validated data, the method further comprising storing the filtered data or the validated data in a computer-readable storage medium.

* * * * *